US012702648B2

(12) United States Patent
Luo et al.

(10) Patent No.: US 12,702,648 B2
(45) Date of Patent: Aug. 11, 2026

(54) TELODENDRIMER NANOCARRIERS FOR MONOMERIC AMPHOTERICIN B DELIVERY

(71) Applicant: The Research Foundation for the State University of New York, Albany, NY (US)

(72) Inventors: Juntao Luo, Syracuse, NY (US); Xiaotian Ji, Syracuse, NY (US); Changying Shi, Syracuse, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 291 days.

(21) Appl. No.: 18/427,037

(22) Filed: Jan. 30, 2024

(65) Prior Publication Data

US 2025/0000811 A1 Jan. 2, 2025

Related U.S. Application Data

(60) Provisional application No. 63/441,993, filed on Jan. 30, 2023.

(51) Int. Cl.

| | |
|---|---|
| ***A61K 9/51*** | (2006.01) |
| ***A61K 31/7048*** | (2006.01) |
| ***A61P 31/10*** | (2006.01) |
| *B82Y 5/00* | (2011.01) |

(52) U.S. Cl.
CPC .......... *A61K 9/5146* (2013.01); *A61K 9/5192* (2013.01); *A61K 31/7048* (2013.01); *A61P 31/10* (2018.01); *B82Y 5/00* (2013.01)

(58) Field of Classification Search
None
See application file for complete search history.

(56) References Cited

U.S. PATENT DOCUMENTS

2015/0056139 A1* 2/2015 Luo .................... A61K 49/0054 424/9.1

* cited by examiner

*Primary Examiner* — Nannette Holloman
(74) *Attorney, Agent, or Firm* — Peter Fallon

(57) ABSTRACT

Systemic fungal infections are an increasingly prevalent health problem. Amphotericin B (AmB), a hydrophobic polyene antibiotic, remains the drug of choice for life-threatening invasive fungal infections. Embodiments disclosed herein are directed telodendrimer (TD) nanocarriers having freely engineered core structures for AmB encapsulation to reduce AmB aggregation status. The reduced aggregation status correlates with the optimized antifungal activity and the attenuated hemolytic properties, as well as reduced cytotoxicity to mammalian cells. The disclosed optimized TD nanocarrier for monomeric AmB encapsulation significantly increases the therapeutic index and reduces the in vivo toxicity and enhances antifungal effects in mouse models with *C. albicans* infection in comparison to two common clinical formulations, i.e., Fungizone and AmBisome.

20 Claims, 30 Drawing Sheets

| | Fungizone | AmBisome | $PEG^{5k}C17_4$ | $PEG^{5k}CHO_4$ | $PEG^{5k}VE_4$ | $PEG^{5k}OA_4$ | $PEG^{5k}CA_8$ | $PEG^{5k}dCA_4$ | $PEG^{10k}C17_4$ |
|---|---|---|---|---|---|---|---|---|---|
| Size of TD (nm) | — | — | 38.9±1.6 | 17.0±2.1 | 24.2±4.3 | 10.3±1.2 | 19.9±1.3 | 8.2±1.6 | 24.0±2.9 |
| Size of AmB-NP (nm) | 40.8±1.5 | 84.1±1.0 | 42.3±4.31 (10:1,TD:AmB) | 26.0±1.7 (10:1,TD:AmB) | 41.0±2.4 (10:1,TD:AmB) | 27.0±2.6 (10:1,TD:AmB) | 46.8±2.6 (10:1,TD:AmB) | 31.4±2.9 (10:1,TD:AmB) | 67.8±2.1(10:1,TD:AmB) 45.2±2.3(20:1,TD:AmB) 41.2±2.4(30:1,TD:AmB) |

FIG. 2a

PEG^5k C17_4
38.9±1.6 nm

Volume (Percent)
20
15
10
5
0
1
10
100
1000
Size (d.nm)

AmB-PEG^5k C17_4 (1:10)
42.3±4.3 nm

Volume (Percent)
20
15
10
5
0
1
10
100
1000
Size (d.nm)

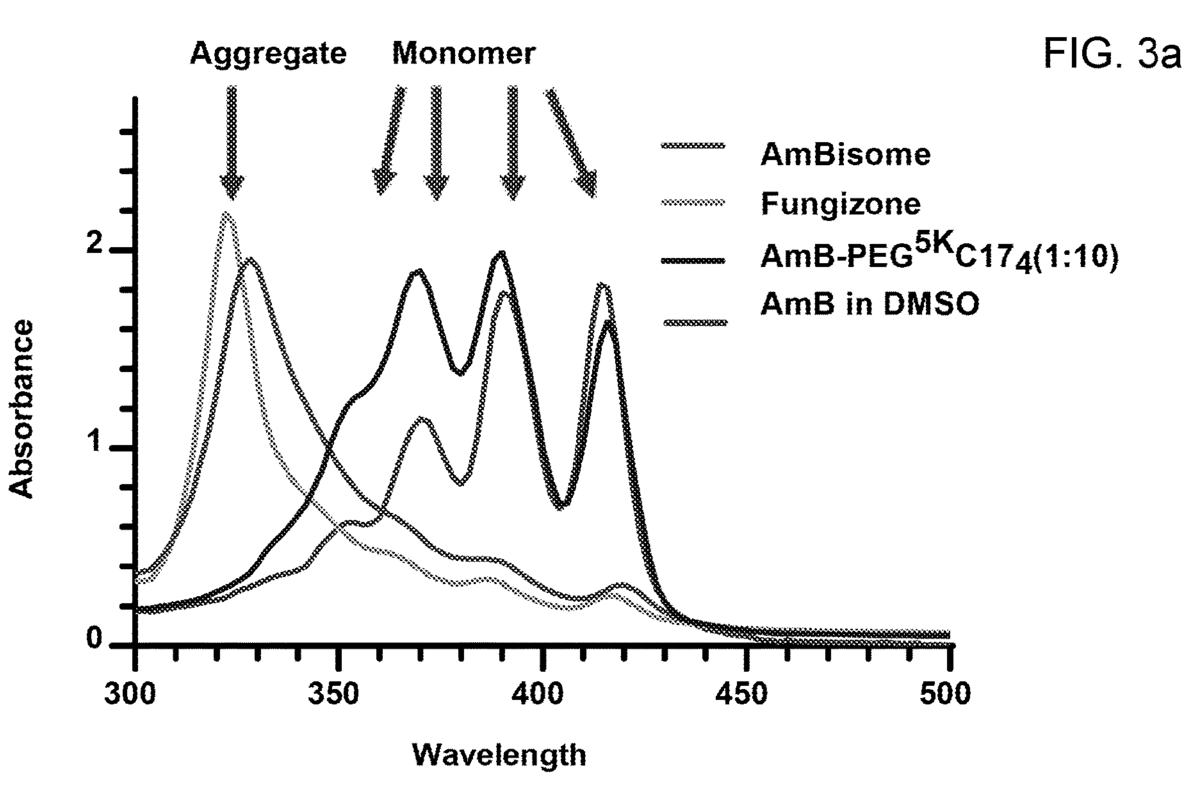
FIG. 3b
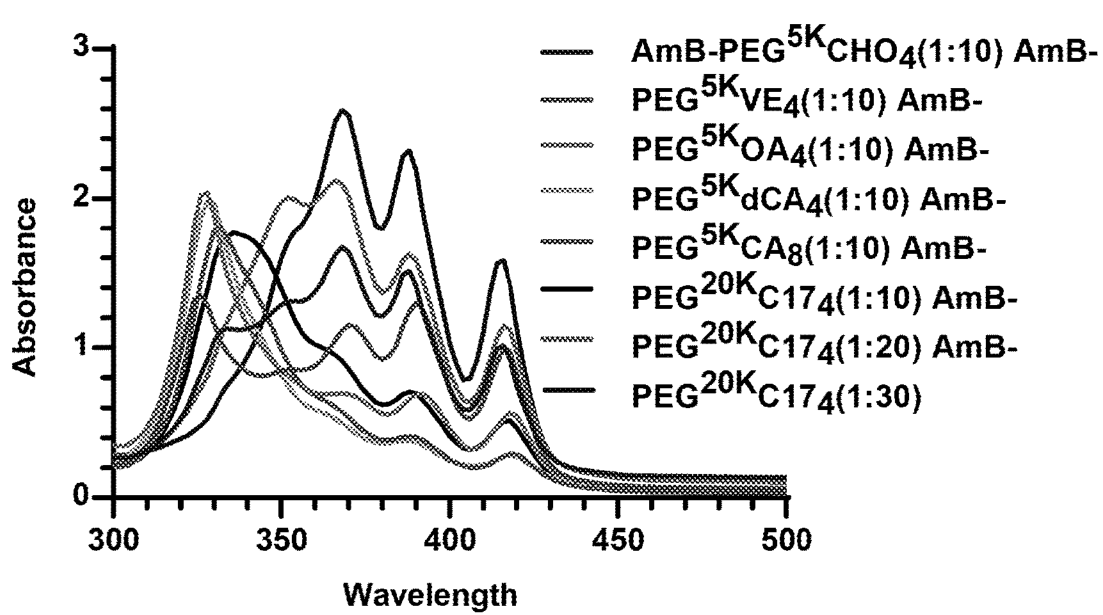

| | Fungizone | AmBisome | $PEG^{5k}C17_4$ | $PEG^{5k}CHO_4$ |
| --- | --- | --- | --- | --- |
| 0.25 | 7.72 | 5.92 | 0.33 | 0.99 (10:1,TD:AmB) |
| $PEG^{5k}VE_4$ | $PEG^{5k}OA_4$ | $PEG^{5k}CA_8$ | $PEG^{5k}dCA_4$ | $PEG^{20k}C17_4$ |
| 1.19 | 3.54 | 8.01 | 8.54 | |

Hemolysis(24h incubation)
Hemolysis (%)
100
50
0
100
50
10
1
Concentration of Drug (μg/mL)
AmB-PEG$^{5k}$dCA$_4$ (1:10)
AmB-PEG$^{5k}$CA$_8$ (1:10)
AmB-PEG$^{5k}$OA$_4$ (1:10)
AmB-PEG$^{5k}$CHO$_4$ (1:10)
AmB-PEG$^{5k}$VE$_4$ (1:10)
AmB-PEG$^{5k}$C17$_4$ (1:10)
AmB-PEG$^{20k}$C17$_4$ (1:20)
AmB
Fungizone
AmBisome AmB-PEG$^{5k}$C17$_4$
AmB-PEG$^{20k}$C17$_4$
Hemolysis (%)
100
80
60
40
20
0
0.0
0.5
1.0
1.5
2
4
6
8
10
A330/A415 ratio of AmB in TD NP
1 μg/ml
10 μg/ml
50 μg/ml
100 μg/ml 1. AmB+Doxil
2. AmB
3. Fungizone+Doxil
4. Fungizone
5. Doxil
6. Doxorubicin 1. AmB-PEG$^{5k}$-dCA$_4$+Doxil
2. AmB-PEG$^{5k}$-dCA$_4$
3. AmB-PEG$^{5k}$-C17$_4$+Doxil
4. AmB-PEG$^{5k}$-C17$_4$
5. AmBisome+Doxil
6. AmBisome
7. Doxil
8. Doxorubicin 1. AmB
2. Doxorubicin
3. Ambisome
4. Doxil
5. AmBisome:Doxil=0.5:1
6. AmBisome:Doxil=1:1
7. AmBisome:Doxil=2:1

| AmB-NP | $PEG^{5k}C17_4$ (10:1,TD:AmB) | $PEG^{5k}dCA_4$ (10:1,TD:AmB) | $PEG^{5k}CHO_4$ (10:1,TD:AmB) | $PEG^{5k}OA_4$ (10:1,TD:AmB) | $PEG^{5k}VE_4$ (10:1,TD:AmB) | $PEG^{5k}CA_8$ (10:1,TD:AmB) | $PEG^{2k}C17_4$ (20:1,TD:AmB) | Fungizone | AmBisome | Free AmB |
|---|---|---|---|---|---|---|---|---|---|---|
| MIC(*C. albicans*, μg/mL) | 0.05 | 0.05 | 0.05 | 0.1 | 0.05 | 0.05 | 0.05 | 0.1 | 0.2 | 0.05 |
| IC50(293T, μg/mL) | 499 | 297 | 352 | 496 | 255 | 106 | 184 | 60 | 330 | 4.3 |
| IC50(RAW, μg/mL) | 205 | 52 | 235 | 146 | 62 | 36 | 165 | 41 | 215 | 1.8 |
| IC50/MIC(293T, μg/mL) | 9980 | 5940 | 7040 | 4960 | 5100 | 2120 | 3680 | 600 | 1650 | 86 |
| IC50/MIC(RAW, μg/mL) | 4100 | 1040 | 4700 | 1460 | 1240 | 720 | 3300 | 410 | 1075 | 36 |

FIG. 5c

Mouse survival after i.v. injection of 2 mg/kg AmB formulations

| Nanoformulations | Survival |
| --- | --- |
| AmBisome | 100 % |
| Fungizone | 33 % |
| AmB-$PEG^{5k}C17_4$ | 100 % |
| AmB-$PEG^{5k}dCA_4$ | 0 % |
| AmB-$PEG^{5k}CHO_4$ | 33 % |
| AmB-$PEG^{5k}VE_4$ | 0 % |
| AmB-$PEG^{5k}OA_4$ | 75 % |
| AmB-$PEG^{20k}C17_4$ | 67% |

Lung
Heart
Liver
Kidney
Spleen
Blood
CFU/g tissue
****
**
*
0
2×10³
4×10³
6×10³
8×10³
1.2×10⁴
1.6×10⁴
1×10³
3×10³
5×10³
1×10⁴
1.5×10⁴
2×10⁴
control
Fungizone
AmBisome
Amb-PEG$^{5K}$-C17$_4$ MeO-PEG-$NH_2$·HCl Fmoc-Lys(Fmoc)-OH
HOBt, DIC, TEA, DMF NHFmoc NHFmoc (1) 20% 4-Methylpiperidine
DMF
(2) Fmoc-Lys(Fmoc)-OH
HOBt, DIC, DMF (1) 20% 4-Methylpiperidine
DMF
(2) Hydrophobic Group
(HG)

FIG. 9

PEG$^{5k}$OA$_4$(Theo.)
PEG$^{5k}$OA$_4$ (by NMR)
e
b
d
a
c
g
f
CO-NH
PEG$^{5k}$OA$_4$
Theo.: 6442.274
Found: 6434.582
6434.582

FIG. 11a
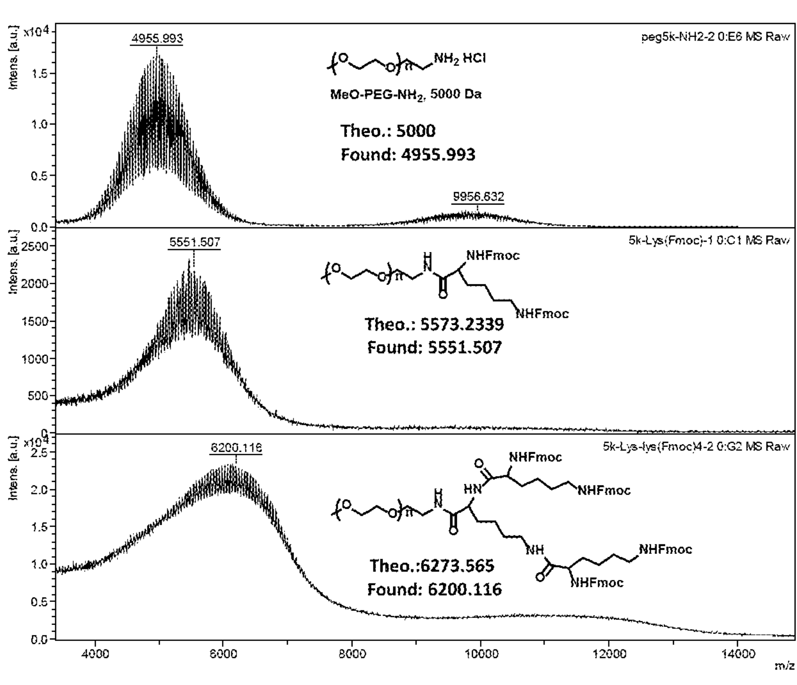
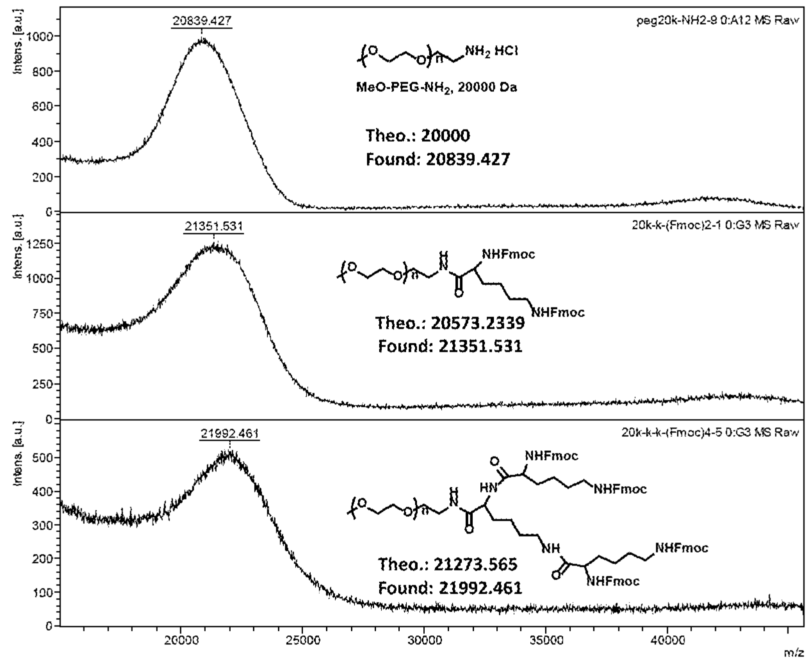
FIG. 11b

Absorbance
Wavelength (nm)
2.0
1.5
1.0
0.5
0.0
300
400
500
600
100% DMSO
80% DMSO
70% DMSO
60% DMSO
50% DMSO
40% DMSO
30% DMSO
20% DMSO
10% DMSO
5% DMSO

A330/A415
DMSO %
4
3
2
1
0
0
20
40
60
80
100

TELODENDRIMER NANOCARRIERS FOR MONOMERIC AMPHOTERICIN B DELIVERY

CROSS-REFERENCE TO RELATED APPLICATIONS

The present disclosure claims priority or the benefit under 35 U.S.C. § 119 of U.S. provisional application No. 63/441,993 filed Jan. 30, 2023, entirely incorporated by reference.

GOVERNMENT SUPPORT CLAUSE

This invention was made with government support under grant number GM130941 and HL139824, awarded by the National Institute of Health. The government has certain rights in the invention.

FIELD OF THE INVENTION

The present disclosure is directed to a drug delivery system suitable for treating subjects in need thereof. For example, a nanotechnology drug delivery system of the present disclosure is suitable for delivering a drug, such as Amphotericin B and/or derivatives thereof to a subject in need. In embodiments, the present disclosure provides a nanoparticle including one or more conjugates of the present disclosure, methods of using the nanoparticles for drug delivery, and treating a disease such as fungal infections.

BACKGROUND

Systemic fungal infections are an increasingly prevalent health problem. Amphotericin B (AmB), a hydrophobic polyene antibiotic, remains the drug of choice for life-threatening invasive fungal infections. However, it has dose-limiting side effects including nephrotoxicity.

Amphotericin B (AmB) is a natural polyene antibiotic with broad spectra of activity for life-threatening systemic fungal infections. The mechanism of action of AmB is based on the affinity of the hydrophobic polyene section with ergosterol in fungal cell membranes causing the increased membrane permeability. A classical barrel-stave model has been proposed decades ago to explain the antifungal effects of AmB through pore formation by oligomeric AmB-ergosterol complexation. A recent NMR and molecular dynamics study suggest that AmB assembles into seven-molecule ion channels. The leakage of intracellular potassium and other contents through the pore causes cell death. The aggregation status of AmB is known to correlate with both antifungal activity and hemolytic property, as well as the dose-limiting nephrotoxicity. The aggregated AmB is more toxic to mammalian cells due to the increased affinity with cholesterol; while the monomeric AmB exhibits high ergosterol selectivity with low cytotoxicity to the host. It is evidenced in the clinical AmB formulations: Fungizone®, which is a conventional sodium deoxycholate micellar formulation of AmB with high degree of AmB aggregation and exhibits high nephrotoxicity and infusion-related reactions. Clinically approved liposomal formulations of AmB, e.g. AmBisome, reduces AmB toxicity, but has not offer better efficacy in the clinic. Instead, the stable drug loading in AmBisome reduces the drug availability, thus requiring higher dose in the clinic for effective antifungal treatment. It significantly increases the cost from both drug and the expensive liposomes. Further, AmBisome is still associated with significant nephrotoxicity at the high dose (10 mg/kg/day).

Numerous nanoformulations have been developed for AmB delivery to improve the efficacy and reduce toxicity and cost in comparison to Fungizone and AmBisome. The common strategy to reduce the toxicity of AmB is to increase the monomeric portion of AmB by limiting the hydrophobic interactions of AmB molecules. Lipid chain containing nanoparticles (NPs) have revealed the reduced AmB aggregation. However, a systematic approach/system is still lacking to enable the fine-tuning of AmB aggregation in nanocarrier to optimize AmB formulation for clinical translation.

Prior-art-of-interest includes: U.S. Patent Publication No. 20150056139 relating to telodendrimers and nanocarriers and methods of using the same; U.S. Patent Publication No. 20190112423 relating to reversibly cross-linked micelle systems; WO2010/039496 relating to a nanocarriers having an interior and an exterior, the nanocarriers including at least one conjugate, wherein each conjugate includes polyethylene glycol (PEG) polymer; WO2013/096388 and WO2012/158622 relating to amphiphilic telodendrimers that aggregate to form nanocarriers characterized by hydrophobic core and a hydrophilic exterior (all of which are entirely incorporated herein by reference).

There remains a need for improved AmB antifungal activity and reduced AmB toxicity both in vitro and in vivo in comparison to Fungizone and AmBisome, which is promising for clinical translation with the increased therapeutic window and the reduced cost.

BRIEF SUMMARY

Embodiments disclosed herein are directed to a novel nanocarrier drug delivery system. The novel nanocarrier drug delivery system contains a PEGylated linear telodendrimer, one or more hydrophobic groups on a dendritic periphery of the telodendrimer, and the nanocarrier having a core structure containing a plurality of micelles and at least one hydrophobic polyene therapeutic agent. In a further embodiment the PEGylated linear telodendrimer comprises oxyethylene repeating units having the following formula: $PEG^{5k}$-$PEG^{20k}$ $H(OCH_2CH_2)_nOH$, wherein n represents number of units. The telodendrimer of the nanocarrier drug delivery system has branching units and the branching units are selected from the group consisting of: 2,6-diaminohexanoic acid (poly-lysine), 2,3-diamino propanoic acid, 2,4-diaminobutanoic acid, 2,5-diaminopentanoic acid (ornithine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid branching units.

Additional embodiments provide that the dendritic periphery comprises one or more hydrophobic groups, such as, heptadecanoic acid (C17), oleic acid (OA), cholesterol (CHO), vitamin E (VE), deoxycholic acid (dCA), and lysine-cholic $acid_2$ ($lysCA_2$). In a particular embodiment disclosed herein, the hydrophobic polyene therapeutic agent is amphotericin B (AmB). According to yet other embodiments, the PEGylated linear telodendrimer is $PEG^{5k}C17_4$ has a hydrodynamic particle size of about 38.9 nm±1, and the hydrophobic polyene therapeutic agent, i.e., amphotericin B (AmB) has a hydrodynamic particle size of about size and 42.3 nm±4.31. According to another embodiment, the ratio of telodendrimer to AmB in the nanocarrier drug delivery system is about 10:1.

Embodiments disclosed herein are directed to a method of treating a subject in need thereof, by injecting the disclosed nanocarrier drug delivery system into a subject in need thereof. Further embodiments are directed to methods of treating systemic fungal infections utilizing the disclosed nanocarrier drug delivery system and pharmaceutically acceptable forms of the disclosed nanocarrier drug delivery system utilizing therapeutically acceptable amounts of AmB.

Other embodiments disclosed herein are directed to methods of making the disclosed nanocarrier drug delivery system utilizing a PEGylated telodendrimer, a dendritic polymer having branched polymers containing a focal point, a plurality of branched monomer units, and a plurality of hydrophobic end groups to provide a core structure containing a plurality of micelles and at least one hydrophobic polyene therapeutic agent.

Embodiments disclosed herein detail the nanocarrier drug delivery system's reduced cytotoxicity, increased antifungal potency, economical production and its increased efficacies over the existing drug alternatives, such as, for example FungiZone and AmBisome.

BRIEF DESCRIPTION OF DRAWINGS

FIG. 2*a* presents hydrodynamic particle sizes of TDs and AmB loaded TD nanoparticles and AmBisome and Fungizone measured by DLS.

FIG. 3*a* presents UV-Vis absorption spectra of AmB in clinical used AmBisome and Fungizone, compare with AmB-$PEG^{5k}C17_4$ (1:10 mass ratio) in PBS (pH 7.4) and free AmB in DMSO; FIG. 3*b* presents UV-Vis absorption spectra of AmB in different TDs at AmB concentration of 1 mg/ml.

FIG. 9 presents synthetic route for the telodendrimers (TDs) with hydrophobic drug binding groups.

FIG. 10*a-f* presents $^1$H NMR in DMSO-de and MALDI-TOF MS spectra of: FIG. 10*a* $PEG^{5k}C17_4$, FIG. 10*b* $PEG^{5k}CHO_4$, FIG. 10*c* $PEG^{5k}VE_4$, FIG. S2*d* $PEG^{5k}dCA_4$, FIG. 10*e* $PEG^5OA_4$ and FIG. 10*f* $PEG^{20k}C17_4$.

FIG. 11*a-b* MALDI-TOF MS spectra of intermediates of solution phase peptide coupling reactions.

DEFINITIONS

Figure 1:
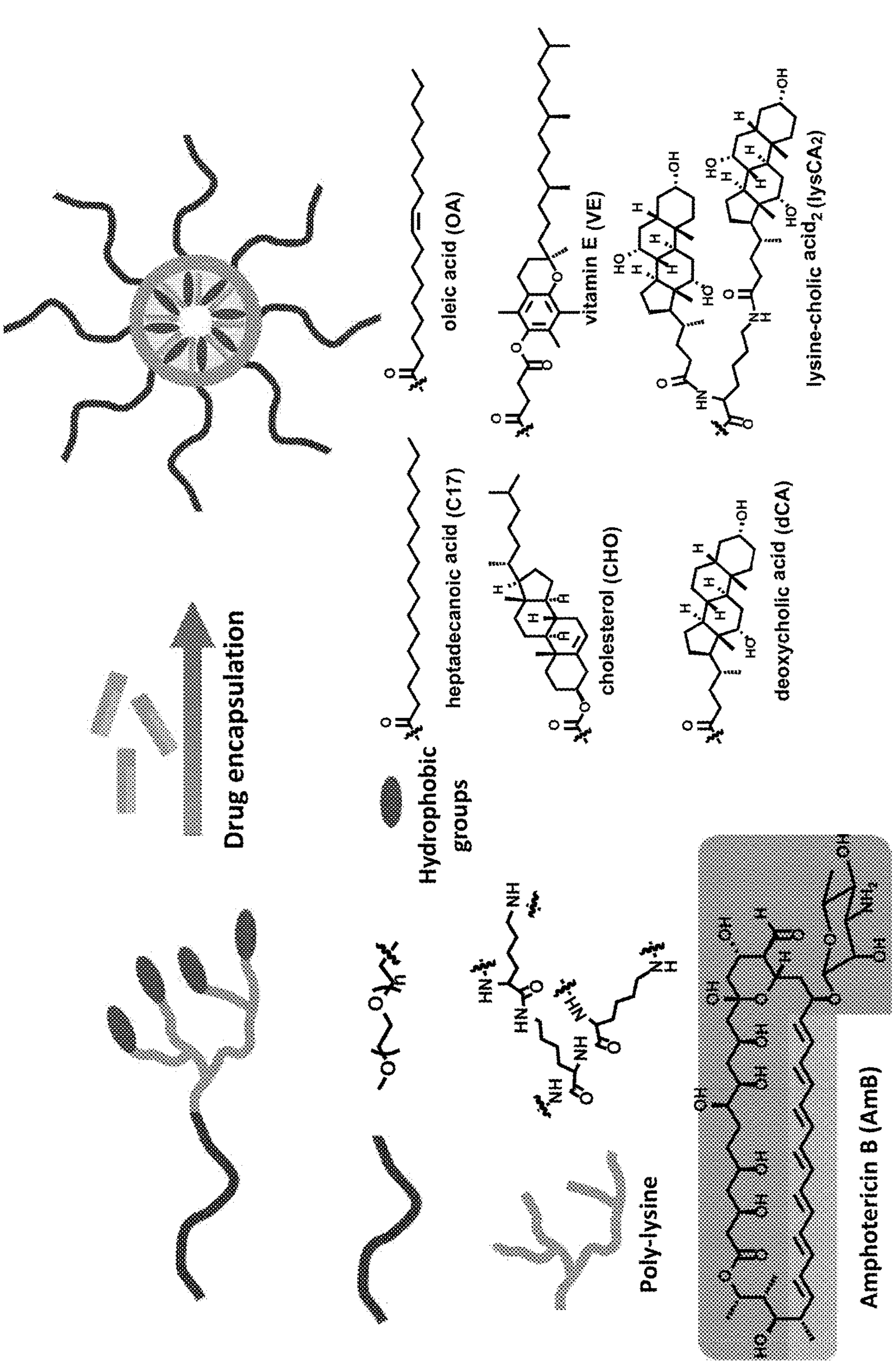
FIG. 1 presents a schematic illustration for the architectures and subunits of TDs for AmB loading.

As used in the present specification, the following words and phrases are generally intended to have the meanings as set forth below, except to the extent that the context in which they are used indicates otherwise.

As used herein, the singular forms "a", "an", and "the" include plural references unless the context clearly dictates otherwise. Thus, for example, references to "a compound" include the use of one or more compound(s).

As used herein the terms "about," "approximately," and the like, when used in connection with a numerical variable, generally refers to the value of the variable and to all values of the variable that are within the experimental error (e.g., within the 95% confidence interval [CI 95%] for the mean) or within +10% of the indicated value, whichever is greater.

As used herein the terms "drug," "drug substance," "active pharmaceutical ingredient," and the like, refer to a compound that may be used for treating a subject in need of treatment.

As used herein the term "excipient" or "adjuvant" refers to any inert substance.

As used herein the terms "drug product," "pharmaceutical dosage form," "dosage form," "final dosage form" and the like, refer to a pharmaceutical composition that is administered to a subject in need of treatment and generally may be in the form of inhalers, tablets, capsules, sachets containing powder or granules, liquid solutions or suspensions, patches, and the like.

As used herein the term "pharmaceutically acceptable" substances refers to those substances, which are within the scope of sound medical judgment suitable for use in contact with the tissues of subjects without undue toxicity, irritation, allergic response, and the like, and effective for their intended use.

As used herein the term "pharmaceutical composition" refers to the combination of one or more drug substances, one or more excipients, and one or more pharmaceutically acceptable vehicles with which the one or more drugs is administered to a subject.

As used herein, the term "telodendrimer" refers to a dendrimer containing a hydrophilic PEG segment and one or more chemical moieties covalently bonded to one or more end groups of the dendrimer. These moieties can include, but are not limited to, hydrophobic groups, hydrophilic groups, amphiphilic compounds, and drugs. Different moieties may be selectively installed at desired end groups using orthogonal protecting group strategies.

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendritic polymer can be attached to other segments of the telodendrimers, and the end groups may be further functionalized with additional chemical moieties.

As used herein, the terms "monomer" and "monomer unit" refer to repeating units that make up the dendrons of the dendritic polymers of the invention. The monomers may be AB2-type monomers, where A and B are two different functional groups capable of reacting together such that the resulting polymer chain has a branch point where an A-B bond is formed. Exemplary monomers include a diamino carboxylic acid, a dihydroxy carboxylic acid and a hydroxyl amino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present invention include, but are not limited to, glyceric acid, 2,4-dihydroxybutyric acid, and 2,2-bis(hydroxymethyl) propionic acid. Examples of hydroxyl amino carboxylic acids include, but are not limited to, serine and homoserine. One of skill in the art will appreciate that other monomer units are useful in the present invention.

As used herein, the term "amino acid" refers to a carboxylic acid bearing an amine functional group. Amino acids include the diamino carboxylic acids described above. Amino acids include naturally occurring .alpha.-amino acids, wherein the amine is bound to the carbon adjacent to the carbonyl carbon of the carboxylic acid. Examples of naturally occurring .alpha.-amino acids include, but are not limited to, L-aspartic acid, L-glutamic acid, L-histidine, L-lysine, and L-arginine. Amino acids may also include the D-enantiomers of naturally occurring .alpha.-amino acids, as well as .beta.-amino acids and other non-naturally occurring amino acids.

As used herein, the term "lipid" refers to lipid molecules that can include fats, waxes, steroids, cholesterol, fat-soluble vitamins, monoglycerides, diglycerides, triglycerides, phospholipids, sphingolipids, glycolipids, cationic or anionic lipids, derivatized lipids, and the like, as described in detail below. Lipids can form micelles, monolayers, and bilayer membranes.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as cholesterol, and many polymers including, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as poly(ethylene glycol) (PEG).

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid and cholic acid analogs and derivatives, and cholesterol formate.

As used herein, the term "cholic acid" refers to (R)-4-((3R, 5S, 7R, 8R, 9S, 10S, 12S, 13R, 14S, 17R)-3,7,12-trihydroxy-10,13-dimethylhexadecahydro-1H-cyclopenta [a]phenan-thren-17-yl) pentanoic acid. Cholic acid is also known as 3.alpha., 7.alpha., 12.alpha.-trihydroxy-5.beta.-cholanoic acid; 3-.alpha., 7-alpha., 12-.alpha.-Trihydroxy-5-.beta.-cholan-24-oic acid; 17-.beta.-(1-methyl-3-carboxypropyl) etiocholane-3.alpha., 7.alpha., 12.alph-a.-triol; cholalic acid; and cholalin. Cholic acid derivatives and analogs, such as allocholic acid, pythocholic acid, avicholic acid, deoxycholic acid, and chenodeoxycholic acid are also useful in the present invention.

As used herein, the terms "drug" or "therapeutic agent" refers to an agent capable of treating and/or ameliorating a condition or disease. Some non-limiting examples of drugs include, paclitaxel, doxorubicin, etoposide, irinotecan, SN-38, cyclosporin A, podophyllotoxin, Carmustine, Amphotericin B, Ixabepilone, Patupilone (epothelone class), rapamycin and platinum drugs. One of skill in the art will appreciate that other drugs are useful in the present invention.

As used herein, "forming a reaction mixture" refers to the process of bringing into contact at least two distinct species such that they mixed together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

As used herein, the term "solvent mixture" refers to a mixture of two or more solvents selected for suspension and/or dissolution of components in a reaction mixture. The solvents in the mixture and the volume ratio in which they are combined depend primarily on the polarity of the lipids and telodendrimers in the reaction mixture. Non-limiting examples of solvents for use in the solvent mixture include chloroform, dichloromethane, ethanol, methanol, acetone, hexanes, petroleum ether, diethyl ether, dioxane, tetrahydrofuran, and water.

As used herein, the term "buffer" refers to an aqueous solution capable of maintaining the pH of the solution at a nearly constant value. The buffer accomplishes this by including a weak acid and its conjugate base, such that the pH does not substantially change following addition of a small amount of acid or base. Representative buffering agents include citric acid, acetic acid, dipotassium phosphate (K.sub.2HPO.sub.4), N-cyclohexyl-2-aminoethanesulfonic acid (CHES), and borate. Buffers commonly used include, but are not limited to, TAPS, bicine, tris, tricine, TAPSO, HEPES, TES, MOPS, PIPES, cacodylate, SSC, MES and succinic acid.

Before embodiments are further described, it is to be understood that this disclosure is not limited to particular embodiments described, as such may, of course, vary. It is also to be understood that the terminology used herein is for the purpose of describing particular embodiments only and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are entirely incorporated herein by reference to disclose and describe the methods and/or materials in connection with which the publications are cited.

DETAILED DESCRIPTION

We have developed a PEGylated linear-dendritic telodendrimer (TD) nanocarrier platform for customized nanocarrier design. We can freely introduce different hydrophobic groups on the dendritic periphery of TD to fine-tune the hydrophobicity and flexibility of the core structure of micelle to control AmB molecular aggregation. We observed that the AmB aggregation status in nanoformulations had a positive correlation with the hemolytic activity and a reverse correlation with antifungal activity. The optimized nanoformulation AmB-PEG$^{5k}$C17$_4$ with the highest monomeric AmB significantly improves the antifungal activities and reduces the toxicity both in vitro and in vivo in comparison to Fungizone and AmBisome, which is promising for clinical translation with the increased therapeutic window and the reduced cost.

The efficacy and toxicity of AmB are directly related to its aggregation state. Here, we report the preparation of a series of telodendrimer (TD) nanocarriers with the freely engineered core structures for AmB encapsulation to fine-tune AmB aggregation status. The reduced aggregation status correlates well with the optimized antifungal activity and the attenuated hemolytic properties and reduced cytotoxicity to mammalian cells. The optimized telodendrimer nanocarrier for monomeric AmB encapsulation significantly increases the therapeutic index and reduces the in vivo toxicity and enhances antifungal effects in mouse models with *C. albicans* infection in comparison to two common clinical formulations, i.e., Fungizone and AmBisome.

Materials: Amphotericin B (AmB, USP grade) was purchased from Gold Biotechnology. Monomethyl-terminated poly(ethylene glycol) monoamine hydrochloride (MeO-PEG-NH2·HCl, Mw 5 kDa) was purchased from Biopharma PEG Scientific Inc. USA. (Fmoc)-Lys (Fmoc)-OH was obtained from Chem-Impex International, Inc. N,N'-diisopropylcarbodiimide (DIC), N-hydroxybenzotriazole (HOBt), N, N-dimethylformamide, anhydrous (DMF, 99.8%), 4-methylpiperidine (99%) and methylene chloride (DCM) were received from Acros Organics. Triethylamine (TEA), D-α-Tocopherol succinate (VE), Amphotericin B solubilized (Fungizone) were purchased from Sigma-Aldrich. AmBisome were obtained from Gilead Sciences, Inc. Heptadecanoic acid (C17, +98%) was purchased from TCI. Cholic acid (CA, +98%), deoxycholic acid (dCA, 99%), oleic acid (OA, 99%) and cholesteryl chloroformate (CHO, 98%) were obtained from Alfa Aesar. Tetrazolium compound [3-(4,5-dimethylthiazol-2-yl)-5-(3-carboxymethoxyphenyl)-2-(4-sulfophenyl)-2H-tetrazolium, MTS] and phenazine methosulfate were purchased from Promega (Madison, WI). *C. albicans* was obtained from the ATCC (ATCC 10231).

Telodendrimer (TD) synthesis: The TDs were synthesized using a solution-phase condensation reaction starting from MeO-PEG$^{5k}$-NH$_2$·HCl (5 kDa or 20 kDa) via stepwise peptide chemistry according to the previous publications. N-terminal-protected lysine was used to synthesize the branched scaffold of TD, N,N'-diisopropylcarbodiimide (DIC) and N-hydroxybenzotriazole (HOBt) were used as coupling reagents. The peptide coupling reactions were carried out with a 3-fold excess of building block and coupling reagents in DMF. The completion of reactions was determined by the negative result of the Kaiser test. PEGylated molecules were precipitated through the addition of the cold ether and then washed with cold ether twice. Fmoc groups were removed by the treatment with 20% (v/v) 4-methylpiperidine in DMF for 30 min, and then precipitated and washed three times by cold ether. White powder precipitate was dried under vacuum. These resulting TDs were dissolved in deionized water, dialyzed against deionized water for 2 days using molecular cutoff ~3.5 kDa dialysis tubing (Thermo Scientific, Rochford, IL), and then dried by lyophilization.

Drug loading and characterization: AmB was encapsulated into the TD micelles by a thin-film hydration method.

The TDs were fully dissolved in $CHCl_3$ and MeOH. AmB was dissolved in DMF and transferred into the TD solutions at certain TD to drug ratios. Solvents were evaporated to dryness and a thin film of homogeneous AmB-TD mixture was coated on the flask wall, which was further dried under a mechanical vacuum for 1 h. Then the film was hydrated in the phosphate buffered saline (PBS, 10 mM, pH 7.4) to form the AmB-TD nanoparticle solutions. All the AmB-TD nanoformulations were covered by the foil during experiments and storage. The particle size distributions and morphology of TDs and drug-loaded nanoformulations were measured by dynamic light scattering (DLS) (Malvern, ZSU5700) and transmission electron microscopy (TEM) (JEM-1400, 80 kV) with negative uranyless staining.

Spectrophotometric analysis of AmB nanoformulations: UV-Vis spectroscopic analysis of various AmB nanoformulations were carried out in the range 300-600 nm on NanoDrop spectrophotometer (NanoDrop 2000c, Thermo Scientific). The monomeric AmB is known to show four absorption peaks at around 350, 368, 388 and 415 nm. The AmB aggregate was determined at around 330 nm. The aggregation state was calculated as the ratio of peak at ~330 nm and peak at ~415 nm. Free AmB, Fungizone, AmBisome and the AmB-TD nanoformulations were scanned at the same AmB concentration (1 mg/mL).

In vitro drug release: The in vitro drug release profiles of AmB nanoformulations were evaluated by dialysis method. The quantification was carried out by UV-Vis spectrophotometer using NanoDrop. In order to determine the release kinetics, a stock solution of AmB nanoformulations were prepared in PBS at concentration 1 mg AmB/mL. The clinically used AmBisome and Fungizone, with equivalent drug concentration were used as comparison. 300 μL of AmB nanoformulations were filled into dialysis cartridges (3.5 kDa MWCO). The cartridge was dialyzed against 50 mL PBS and gently shaken at 37° C. The PBS solution was completely removed at regular time intervals for analysis of drug concentration and replaced with fresh medium. At determined time point, 3 μL samples from dialysis cartridges were withdrawn for drug concentration analysis. AmB concentration was calculated from the standard curve of free AmB or AmB-nanoformulations. Data were reported as the average percentage of AmB accumulative release for triplicated samples.

Hemolysis assay: To determine the hemolytic activity of different nanoformulations, 1 mL of fresh blood from a healthy human volunteer was collected. The blood was added into 5 mL PBS solutions with 20 mM EDTA, followed by centrifugation at 1,000 rpm for 10 minutes to collect the red blood cells (RBCs). Then RBCs were washed by PBS for three times and resuspended into 20 ml of PBS. AmB nanoformulations or blank TDs were added into 200 μL RBC solutions with final concentration at 10, 100, 500 and 1000 μg/mL of TDs (1, 10, 50 and 100 μg/mL of AmB) followed by gentle pipette and incubation at 37° C. The free AmB was dissolved in DMSO and added into RBCs (final 5% DMSO). At determined time point (0.5 h, 4 h and 24 h), the samples were centrifuged at 1000 rpm for 3 min. The hemoglobin in supernatant was analyzed by the UV absorbance at 540 nm. PBS and Triton-100 (2%) were also incubated with RBCs as negative and positive control, respectively. The haemolytic toxicity was calculated by the following equation: Hemolysis $\%=[(OD_{sample}-OD_{PBS})/(OD_{triton}-OD_{PBS})]\times100\%$.

Electrophoresis Assays: The release profiles of doxorubicin from Doxil were investigated using electrophoresis assay. The Doxil with free AmB or AmB nanoformulation were incubated at 37° C. for 24 h and then loaded into the gel. The gel tray was run for 40 min at a constant current of 40 mA. The gel was then imaged by a Universal Hood II Gel imaging system (Bio-Rad Laboratories, Inc.).

In vitro cytotoxicity test: The cytotoxicity of TDs and AmB loaded nanoparticles (NPs) were studied using murine macrophage-like RAW 264.7 cells and human kidney 293T cells via MTS assays. Briefly, cells were seeded in 96-well plates at a density of $6\times10^3$ (RAW 264.7) and $3\times10^3$ (293T) cells per well and incubated overnight (Dulbecco's modified Eagle's medium (DMEM) medium, 5% $CO_2$, 37° C.). TDs or AmB nanoformulations with different concentrations were added into each well to treat the cells. After 72 h incubation, CellTiter 96 AQueous MTS reagent was added to each well according to the manufacturer's instructions. The cell viability was determined by measuring the absorbance at 490 nm using a microplate reader (BioTek Synergy H1) with the untreated cells as negative controls. Results were obtained as the average cell viability of triplicate experiments calculated by a formula of $[(OD_{treat}-OD_{blank})/(OD_{control}-OD_{blank})\times100\%]$.

In vitro antifungal activity: In order to study the influence of encapsulation of AmB in TDs on the antifungal activity of the drug, the minimal inhibitory concentration (MIC), defined as the lowest concentration inhibiting clearly visible growth of the fungi, was determined by dilution method. The antifungal agents were tested at AmB final concentration range of 0.0125-5 μg/mL. The testing was performed in 96-well plates. Cell suspensions of *C. albicans* were prepared in Sabouraud's broth and adjusted to a final concentration of $5\times10^6$ cells/mL (fungal count determined by microscopic counts on a hemocytometer). The 96-well plate was incubated for 24 h at 25° C. and record the lowest concentration of AmB that prevented visible growth of *C. albicans*.

Pharmacokinetics study: In this study, male and female wild type mice (C57BL/6, 6 weeks) purchased from Charles River (USA) were maintained under pathogen-free conditions (22±2° C. and 60% air humidity, 12 h light/dark cycle) according to the AAALAC (Association for Assessment and Accreditation of Laboratory Animal Care) guidelines and were allowed to acclimatize for at least 4 days before any experiments. All animal experiments were performed in compliance with the institutional guidelines and according to the protocol approved by the Committee for the Humane Use of Animals of State University of New York Upstate Medical University (IACUC 437).

Mice were randomly divided into three groups (n=3-5 per group) and intravenously (i.v.) injected with AmBisome, Fungizone or AmB-TD at AmB single dose of 1 mg/kg. Blood samples (50 μL) were collected from mice tail vein at defined time points (5 min, 30 min, 2 h, 4 h, 8 h and 24 h) in Eppendorf tube and centrifuged at 7000 rpm for 5 min to obtain plasma. 20 μL of DMSO and 20 μL of acetone were added into the plasma. After centrifugation (13,300 rpm×2 min), the supernatant was collected and the solvent were evaporated by speed vacuum concentrator (SVC 100H). Finally, 5 μL of DMSO was added to dissolve the drug and the AmB concentration was determined by Nanodrop. The pharmacokinetic parameters were calculated by GraphPad Prism. AUC (area under the curve) and $T_{1/2}$ (half-life) were determined.

In vivo toxicity of AmB nanoformulations: In vivo toxicity of AmB nanoformulations were tested using Wild type C57BL/6 mice. Mice (n=3-4 per group) were given a single i.v. injection of 2 mg of AmB/kg via the tail vein. The animals were monitored daily over a period of 14 days for survival and activity.

In vivo antifungal treatments: In vivo therapeutic efficacy of AmB-TDs was tested in *C. albicans* infection mouse model. One day before the treatment, wild type mice (C57BL/6) were infected by i.v. injection of *C. albicans* through the tail vein with an inoculum of $1.5\times10^7$ cells/kg in PBS. The mice were treated using AmB-TD, AmBisome and Fungizone with three doses at day 1, 4 and 7 (1 mg AmB/kg/dose). PBS injection was used as the control groups with the infected mice. Body weight were monitored for 10 days. On day 10, animals from different treatment groups were sacrificed. Blood and organs (liver, kidney, heart, lung and spleen) from the sacrificed animals were excised. Part of tissue was aseptically homogenized in 10 times of sterile medium. The homogenate was diluted suitably (1/1, 1/10 and 1/100) with Sabouraud's broth medium for plating on Sabouraud dextrose agar (SDA plate). Colony forming units (CFU) were counted after 48 h of incubation at 25° C. The rest of tissue were frozen and sectioned using cryosection machine (LEICA CM1950) with a thickness of 5 μm. The sections were stained by hematoxylin and eosin (H&E) for histopathology analysis.

Statistical analysis: Statistical analysis was carried out using GraphPad Prism (GraphPad Software, California, USA). One-way analyses of variance (ANOVA) was used for two-group and multiple-group analyses. Statistical significance was represented as *: p<0.05; : p<0.01; *: p<0.001; ****: p<0.0001. All data points referred to the mean±standard deviation (SD) and were based on at least three separate experiments (n=3). The half maximal inhibitory concentration (IC50) was calculated by nonlinear regression analysis ([Inhibitor] vs. response—Variable slope (four parameters)). The half-life was determined by nonlinear regression analysis (one-phase association).

Results and Discussion: The amphiphilic feature of AmB leads to the self-assembly of drug molecules in aqueous solution, which lead to the increased binding with cholesterol in mammalian cell membranes and results in mammalian cell toxicity. The control of the aggregation status of AmB in nanoparticle (NP) determines the stability, release profile, efficacy and toxicity of the formulation. In the previous studies, we have developed a well-defined linear PEG-dendritic telodendrimer (TD), which can be precisely engineered for therapeutic delivery. Here we prepared a series of TDs by introducing various hydrophobic groups onto the peripheral of TD using peptide chemistry (FIG. 1) to optimize AmB encapsulation via hydrophobic interactions. Hydrophobic moieties with different rigidity and hydrophobicity were selected to adjust interactions with the polyene group on AmB in order to modulate the aggregation status of AmB, which may impact both release profile and cytotoxicity as reported in the literature. We also introduced AmB-binding cholesterol (CHO) and other sterol compounds, e.g., cholic acid (CA) and deoxycholic acid (dCA) in TD to breakdown AmB aggregates. Hydrophilic PEG chain with various length were included to optimize the stability of the nanoparticles and prevent the unspecific cell membrane binding.

Figure 9:
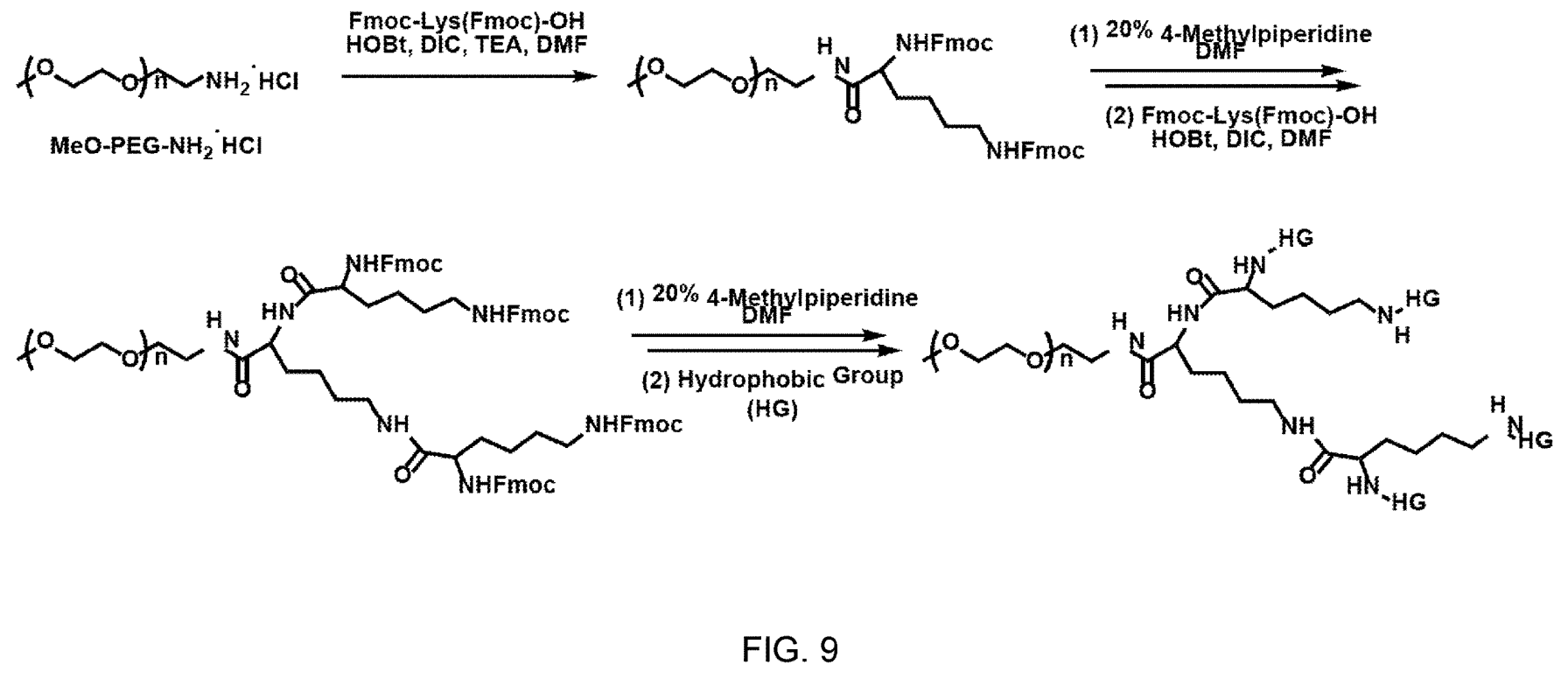
Figure 10A:
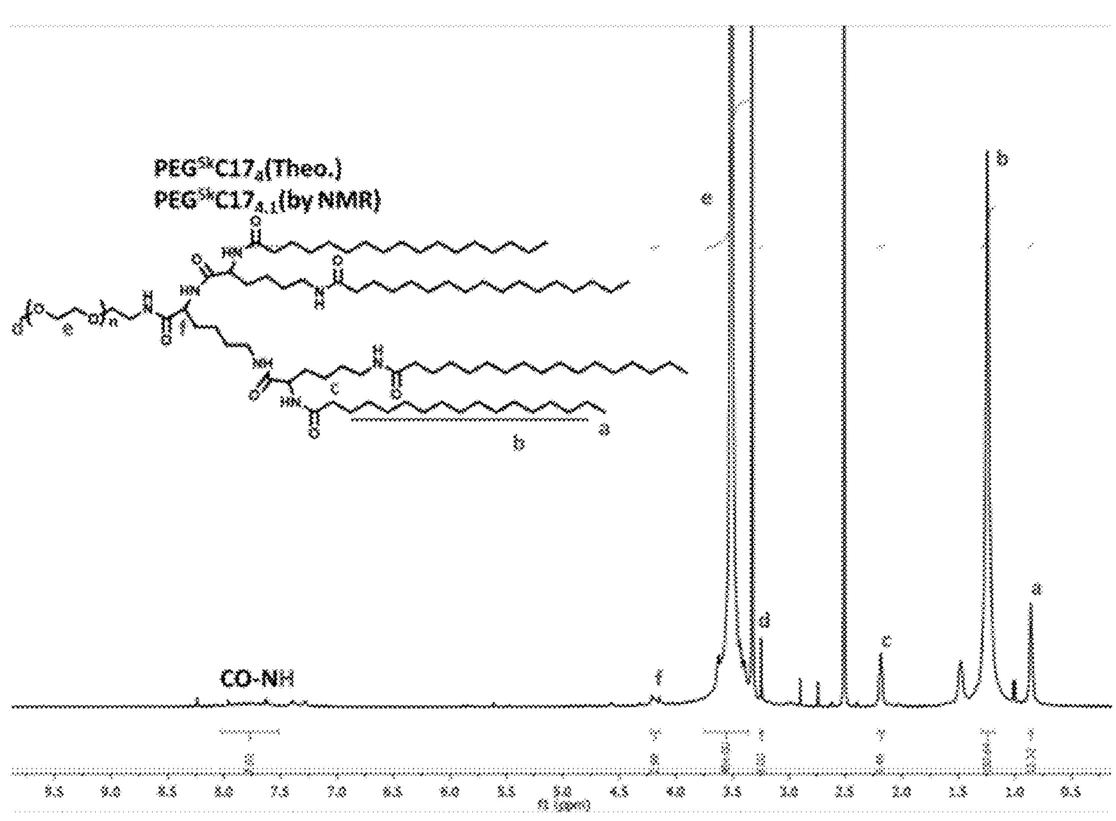
Figure 10A:
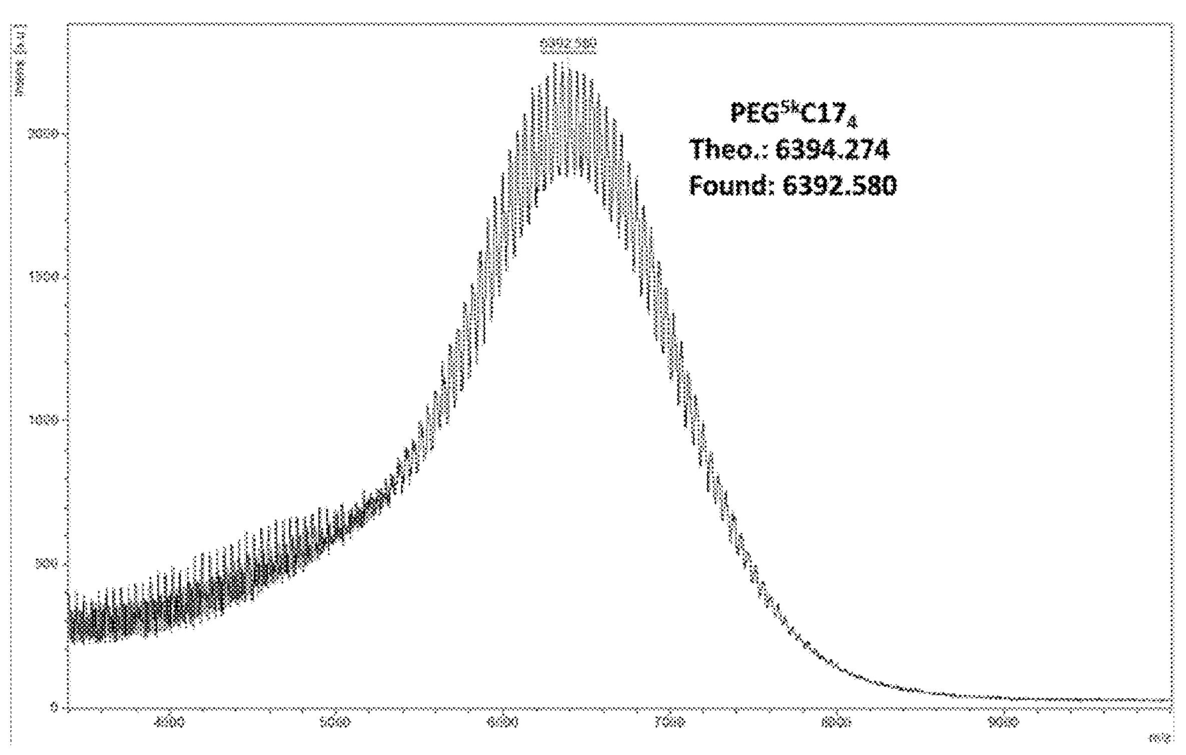
Figure 10B:
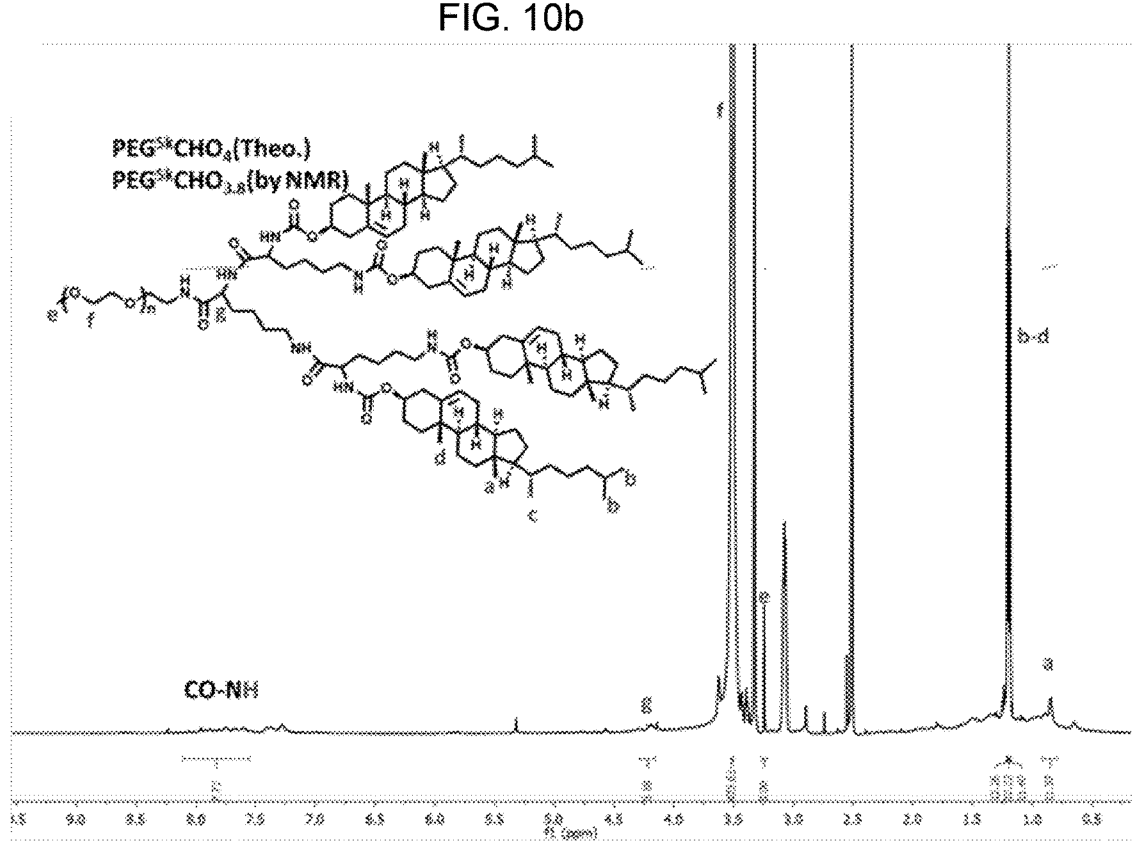
Figure 10B:
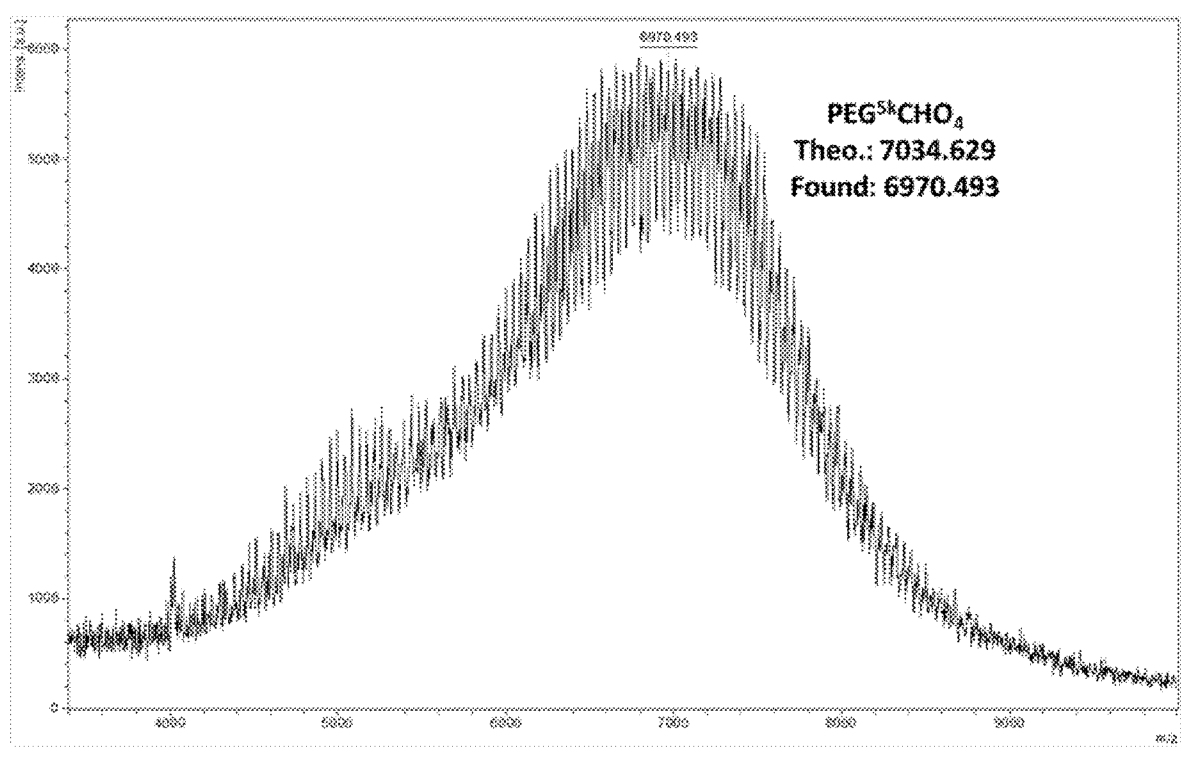
Figure 10C:
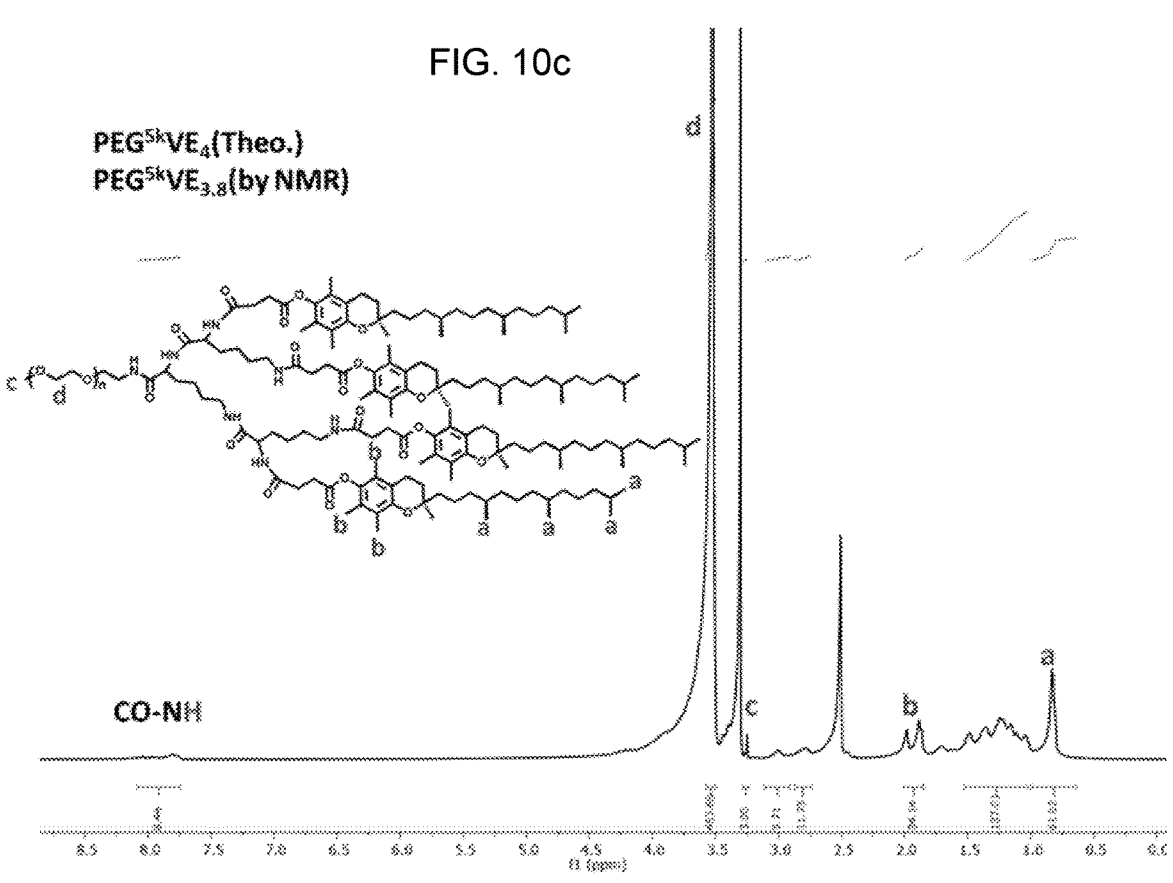
Figure 10C:
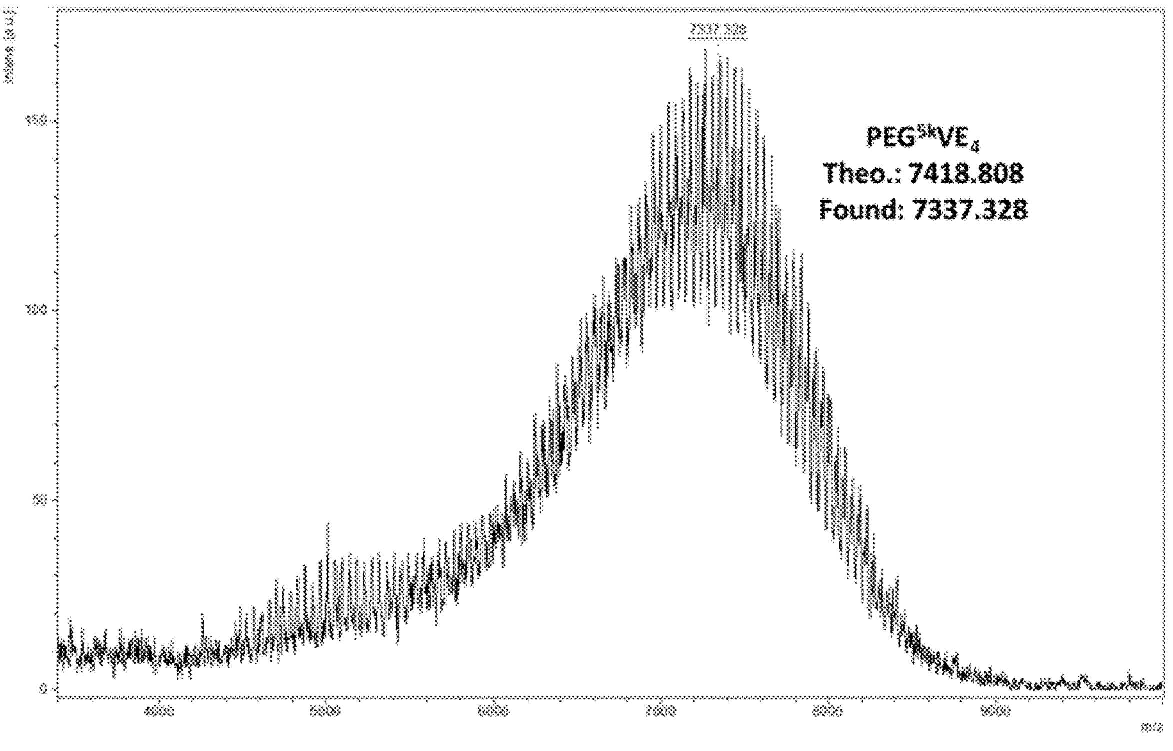
Figure 10D:
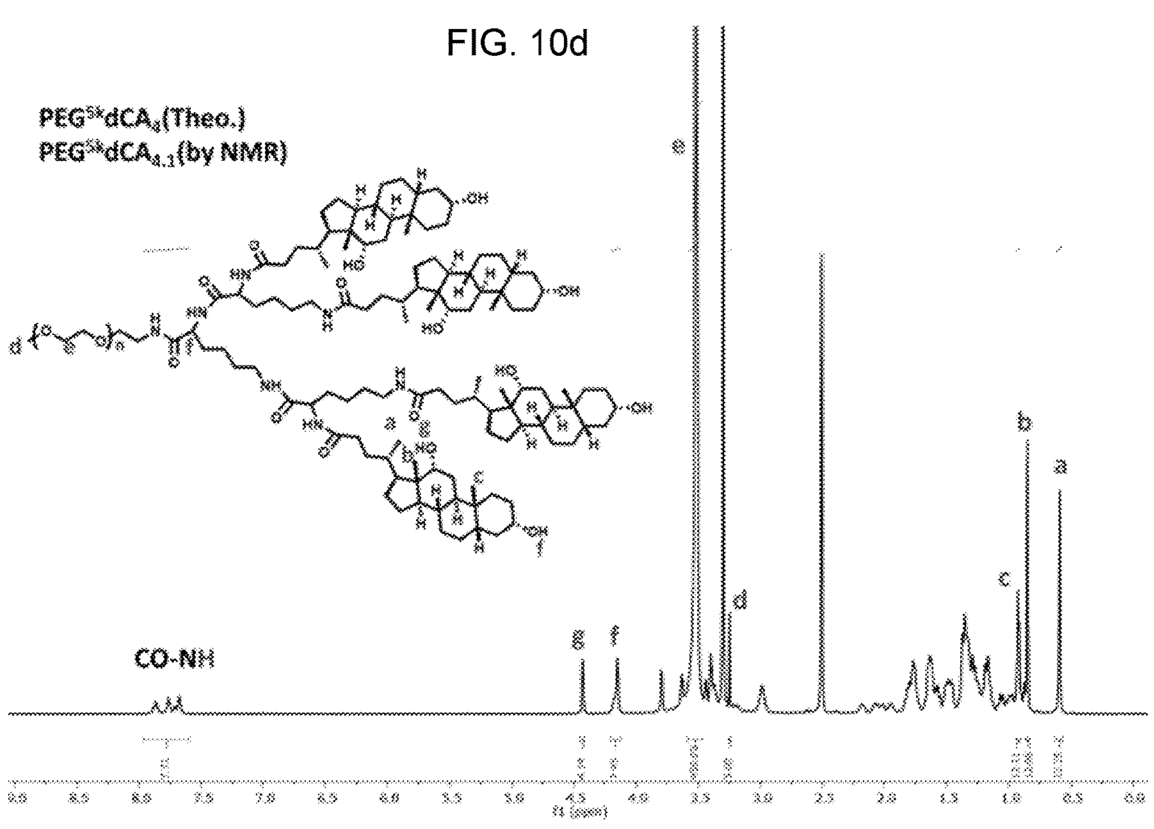
Figure 10D:
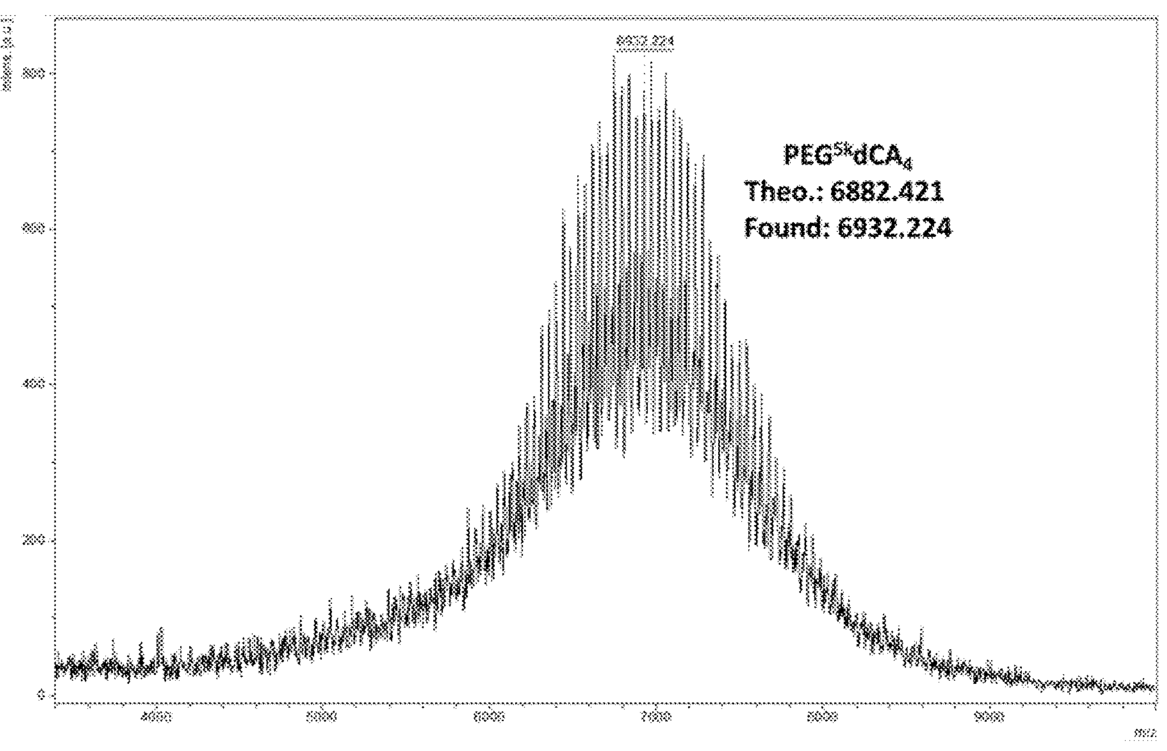
Figure 10E:
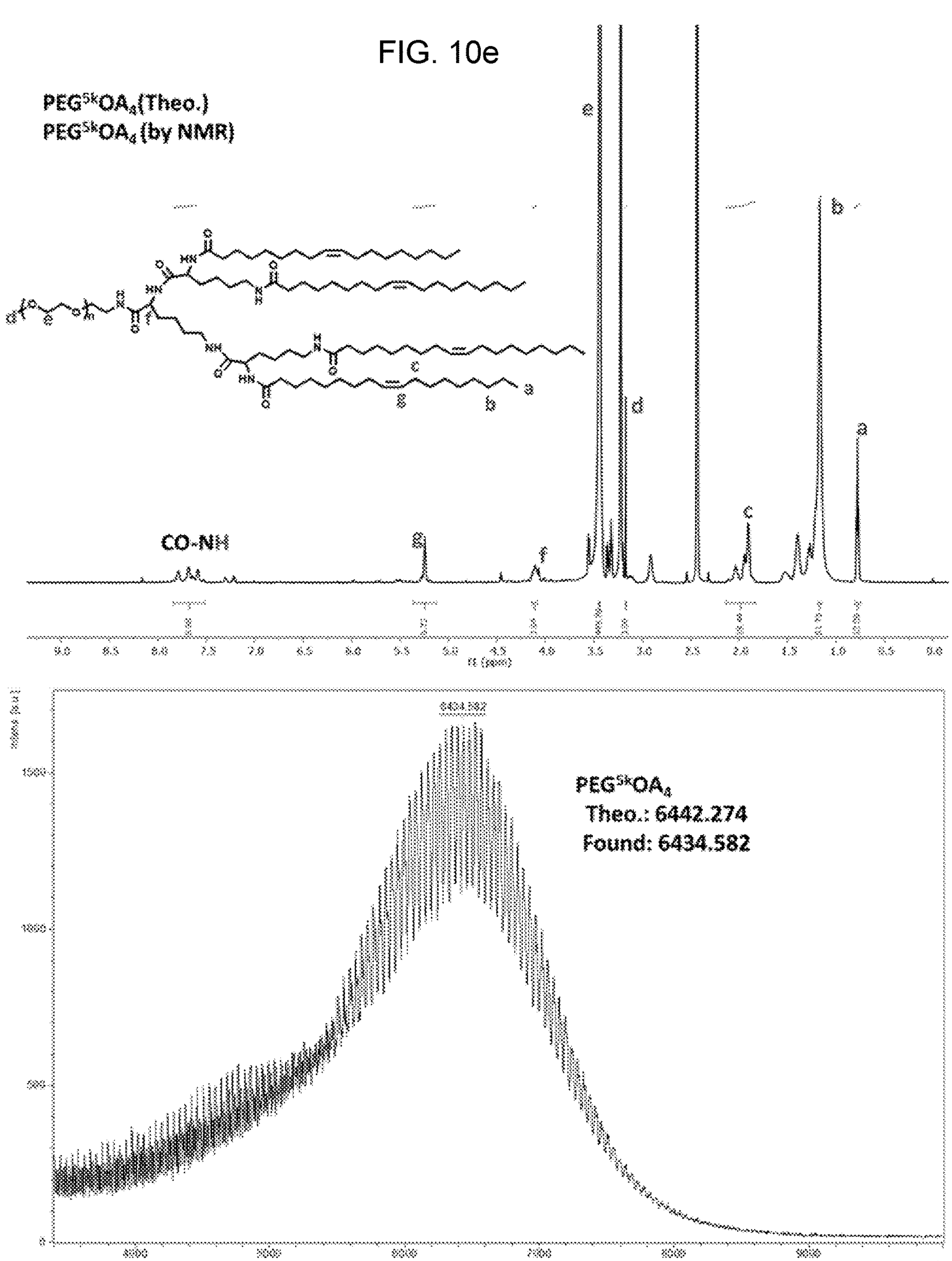
Figure 10F:
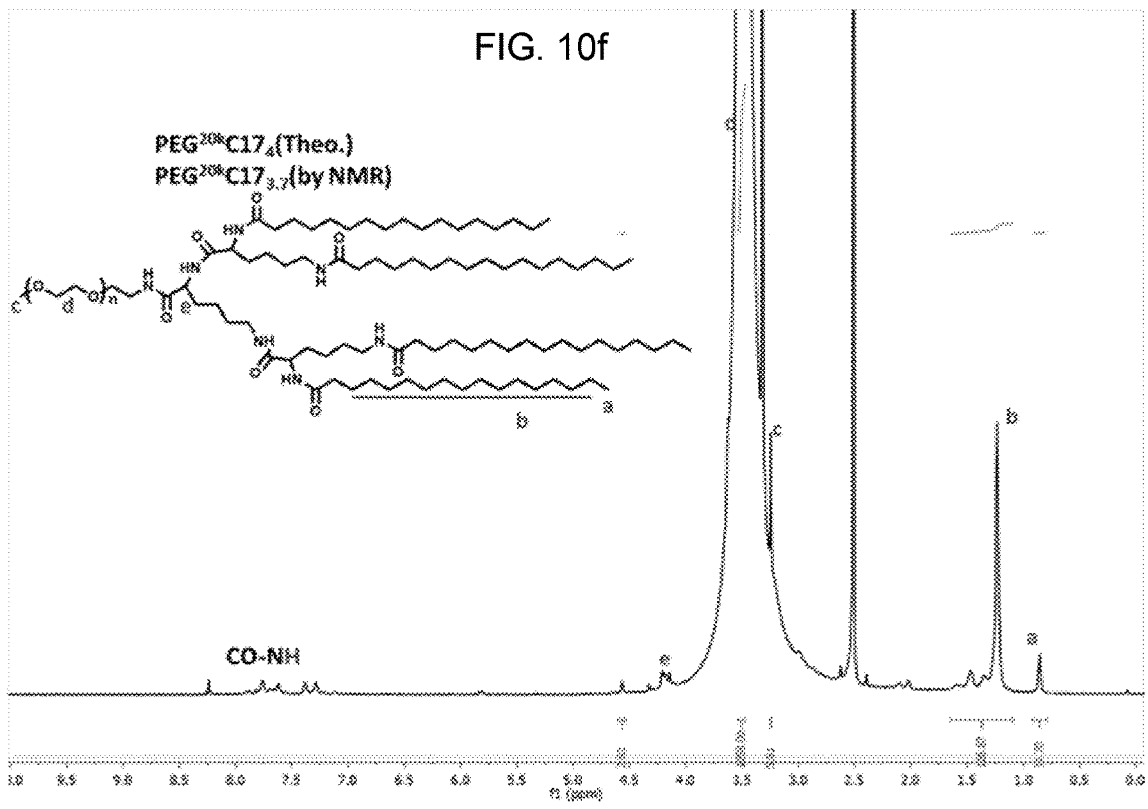
Figure 10F:
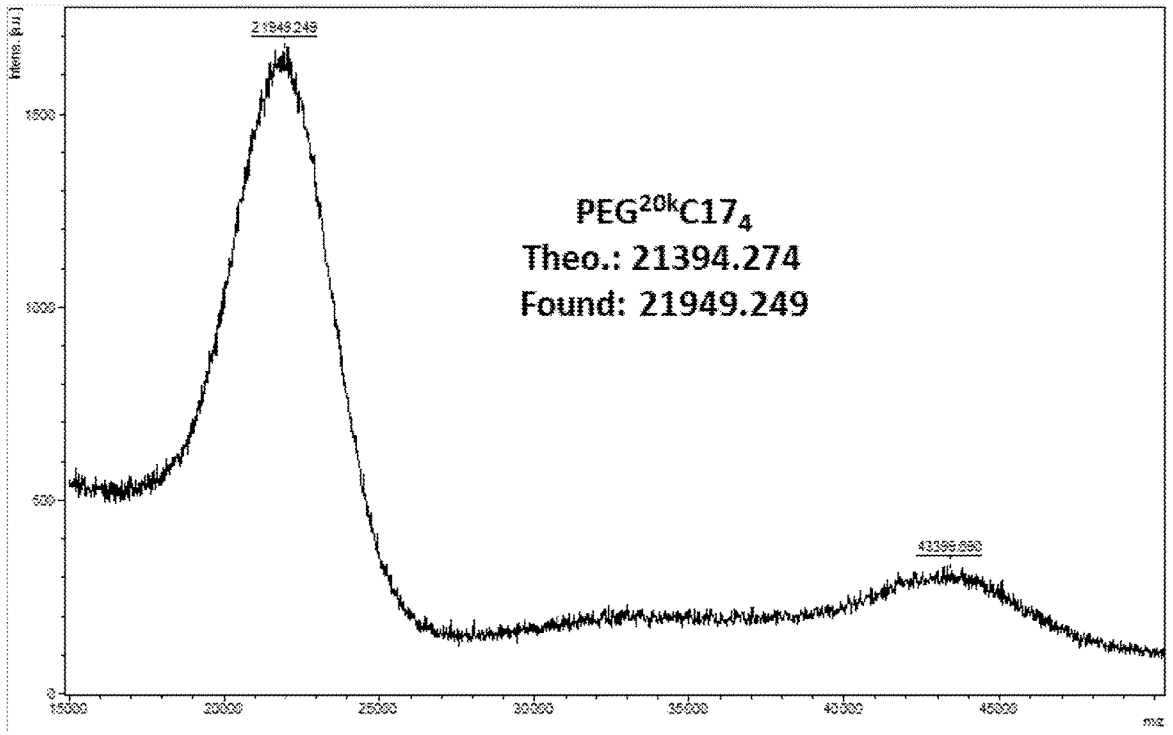
Figure 12:
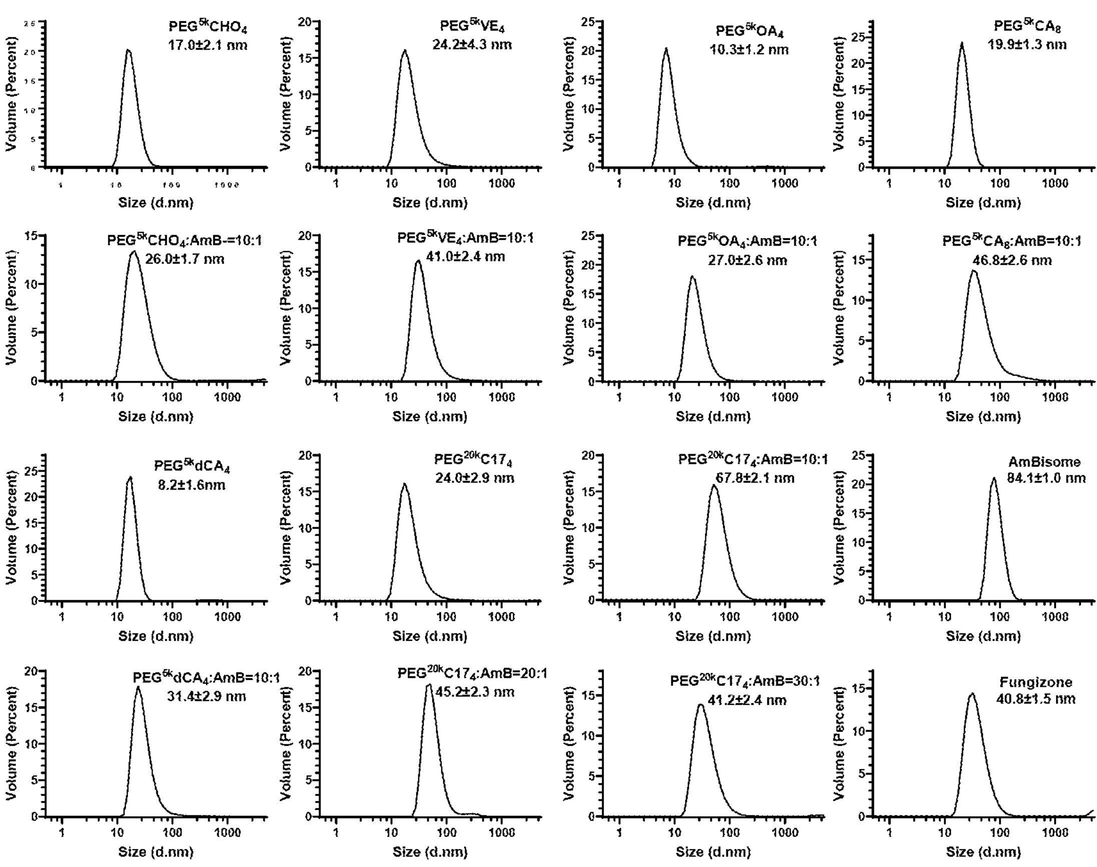
FIG. 12. Hydrodynamic sizes of TD and AmB loaded TD nanoformulations measured by DLS (The data are presented as mean±SD, n=3).

TDs synthesis and characterization: Following the procedure in our previous studies, TDs were synthesized via solution phase peptide coupling reactions starting with MeO-$PEG^{5k}NH_2$. The dendritic poly-lysine scaffold was synthesized by two repeated conjugations of N-Fmoc protected lysine. Finally, heptadecanoic acid (C17), oleic acid (OA), vitamin E (VE), deoxycholic acid (dCA) and cholesterol (CHO) were conjugated on the dendritic periphery to yield TD with multiple hydrophobic moieties (FIG. 9). The chemical structures of TDs were characterized by $^1H$ NMR (FIG. 10). The numbers of hydrophobic groups in the TD were calculated based on the peak integrations of the methyl protons on hydrophobic tails (~0.88, ~0.86, ~0.84, ~0.59 and ~0.78 ppm for C17, CHO, VE, dCA and OA, respectively) by referencing methoxy protons on PEG at ~3.24 ppm in $^1H$ NMR spectra in DMSO-$d_6$. The chemical formulas of TDs were calculated to be very close to the designed structures: $PEG^{5k}C17_{4.1}$, $PEG^{5k}CHO_{3.8}$, $PEG^{5k}VE_{3.8}$, $PEG^{5k}dCA_{4.1}$, $PEG^{5k}OA_{4.0}$ and $PEG^{20k}C17_{3.7}$. Further, the molecular weights of TDs and intermediates were measured via MALDI-TOF MS (FIG. 10*a* f and FIG. 11*a-b*). As show in FIG. 11*a-b*, expected molecular weight increase can be observed after each lysine coupling. The monomodal molecular weight distributions were observed for all TDs with very close molecular weights to the theoretical design. As comparison, $PEG^{5k}CA_8$ with cholic acid as the peripheral building blocks was applied as prepared and characterized in previous studies.

Figure 2B:
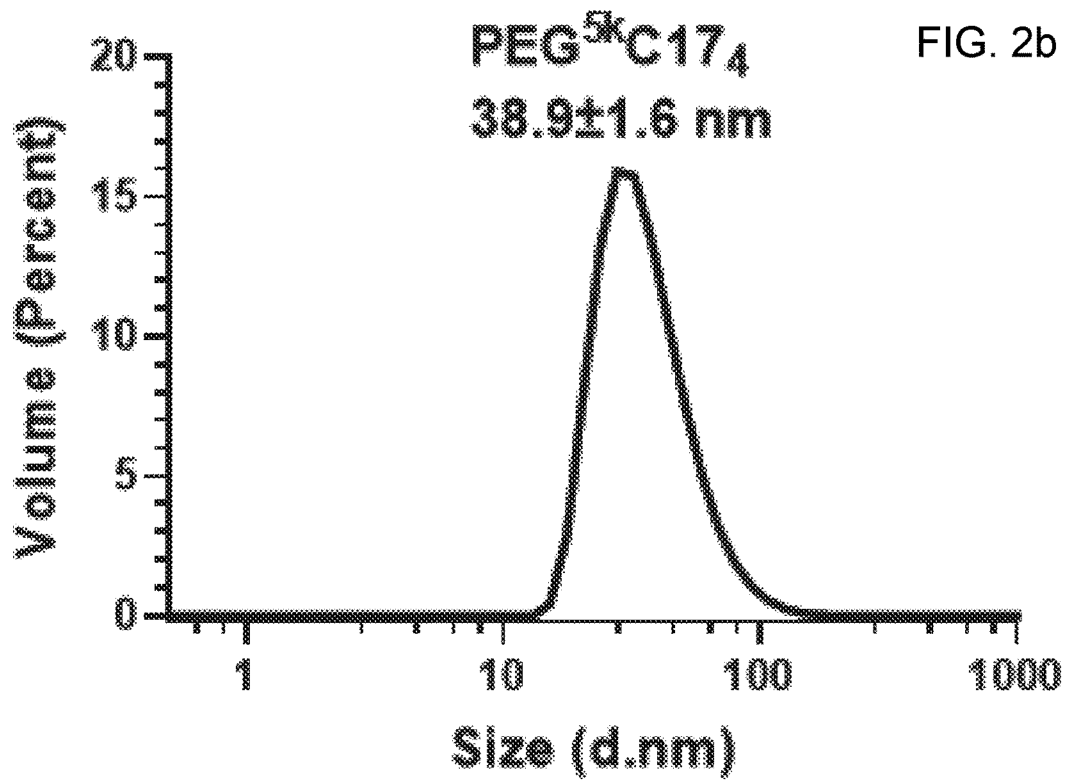
FIGS. 2*b*-2*e* present hydrodynamic size distribution and transmission electron microscopy (TEM) morphological images of a typical TD $PEG^{5k}C17_4$ before (FIG. 2*b*, FIG. 2*d*) and after (FIG. 2*c*, FIG. 2*e*) AmB loading.
Figure 2C:
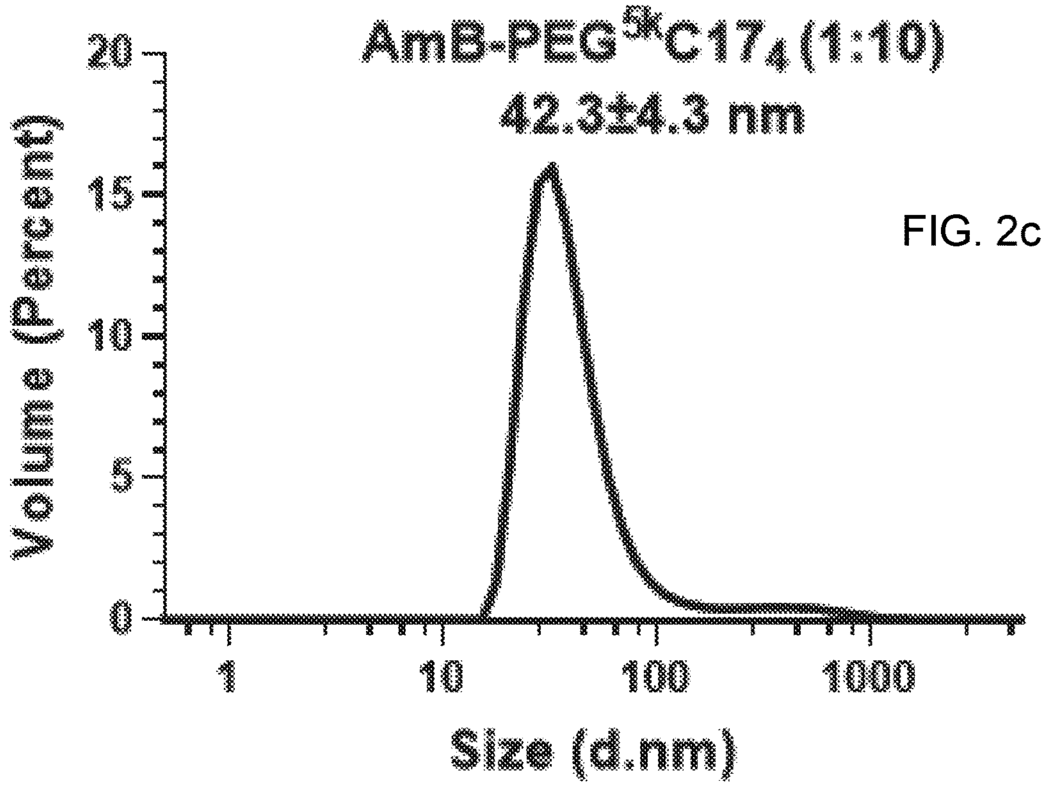
Figure 2D:
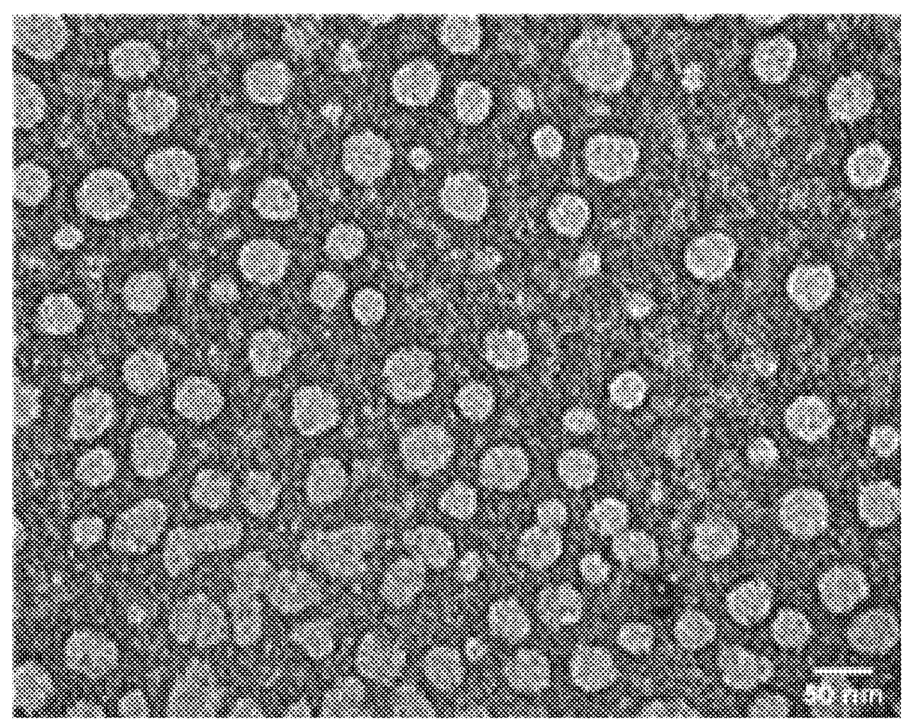
Figure 2E:
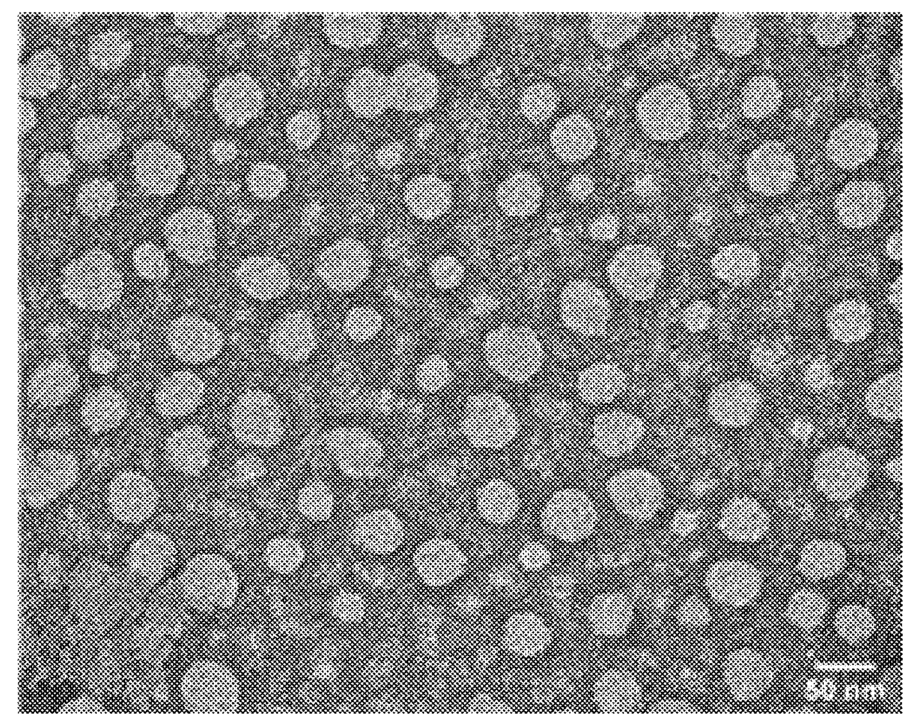
Figure 2F:
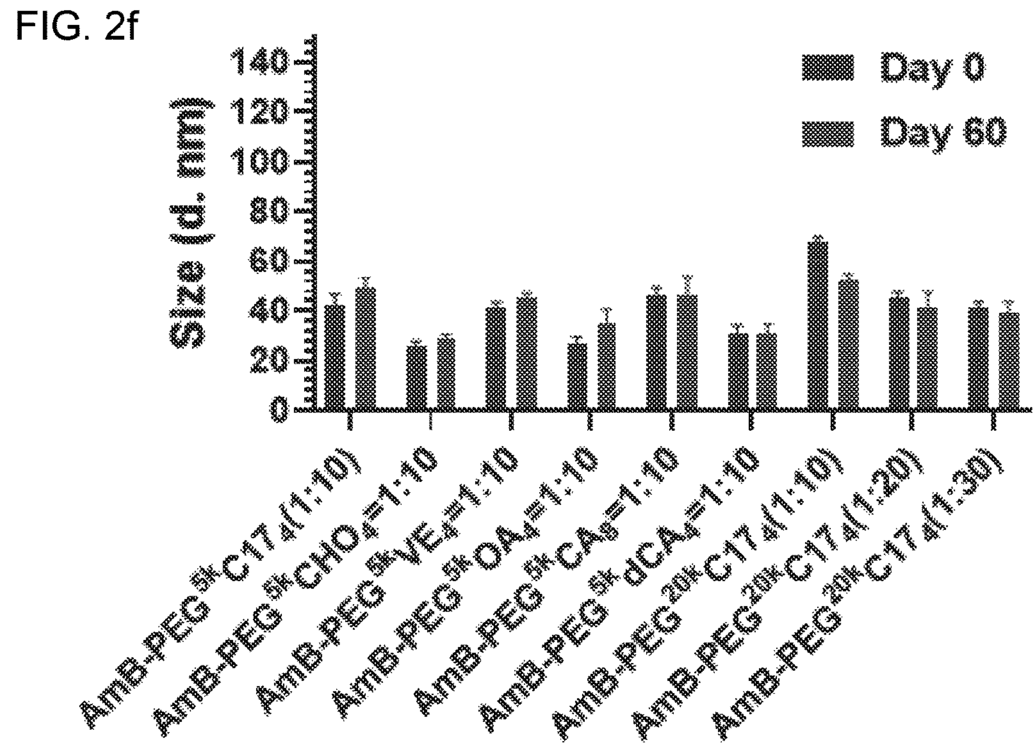
FIG. 2*f* presents the comparison of the hydrodynamic sizes of various AmB-TD nanoformulations before and after storage for 2 months at 4° C.

TDs self-assembled into monodispersed NPs with hydrodynamic diameters of ~10-40 nm (FIG. 2*a* and FIG. S4) in phosphate buffered saline (PBS, 10 mM, pH 7.4) determined by dynamic light scattering (DLS). AmB can be effectively loaded in all TD nanocarriers at a feeding mass ratio of 10:1 TD/drug with almost quantitative loading efficiency without any drug precipitation. The particle sizes are slightly increased after drug loading but remain small in range ~25-47 nm for all TD nanoparticles (FIG. 2*a*). In comparison, Fungizone and AmBisome have larger hydrodynamic particle sizes of 40 nm and 84 nm, respectively, as measured by DLS. The morphology of the nanoparticles was characterized using transmission electron microscopy (TEM). As shown in FIG. 2*d* and FIG. 2*e*, a typical TD $PEG^{5k}C17_4$ has a narrow dispersed and relative uniform spherical particles with size about 35.3±5.8 nm, which is consistent with DLS measurements. The particle sizes of $PEG^{5k}C17_4$ are slightly increased to 39.7±6.3 nm after AmB loading as shown in TEM images. The particle sizes of AmB-TD formulations remains stable after storage for 2 months at 4° C. as shown in FIG. 2*f*.

Figure 2G:
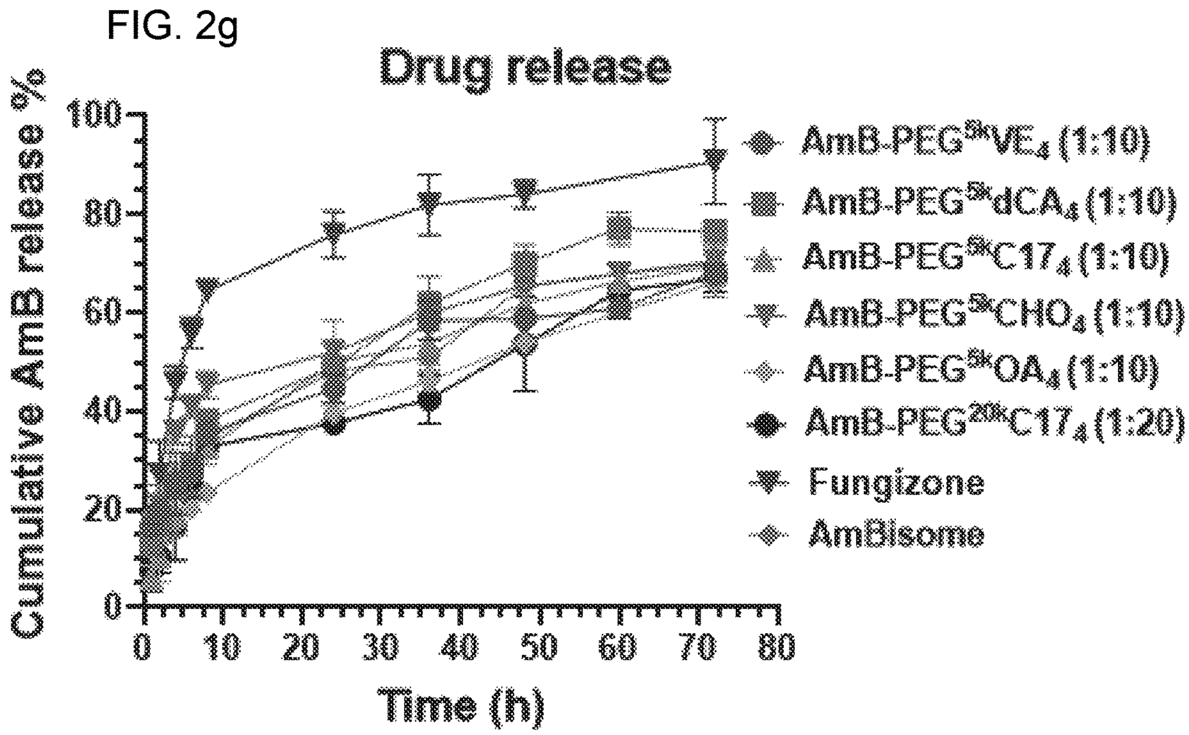
FIG. 2*g* presents AmB release profiles from AmB-TD nanoformulations compared with AmBisome and Fungizone (mean±SD, n=3; TEM scale bar: 50 nm).

The in vitro drug release profiles of the freshly prepared AmB-NPs were characterized using dialysis method in PBS (pH 7.4) for 72 h, and the results are displayed in FIG. 2*g*. The AmB release from Fungizone was determined with an initial burst release of ~65% in the first 8 h and ~90% within 3 days. AmBisome shows a sustainable release profile with an accumulative AmB release of ~70% after 3 days. Similar to AmBisome, the AmB-TD nanoformulations exhibited slower drug-release kinetics, suggesting the reduced toxicity and effective antifungal activity.

Figure 13A:
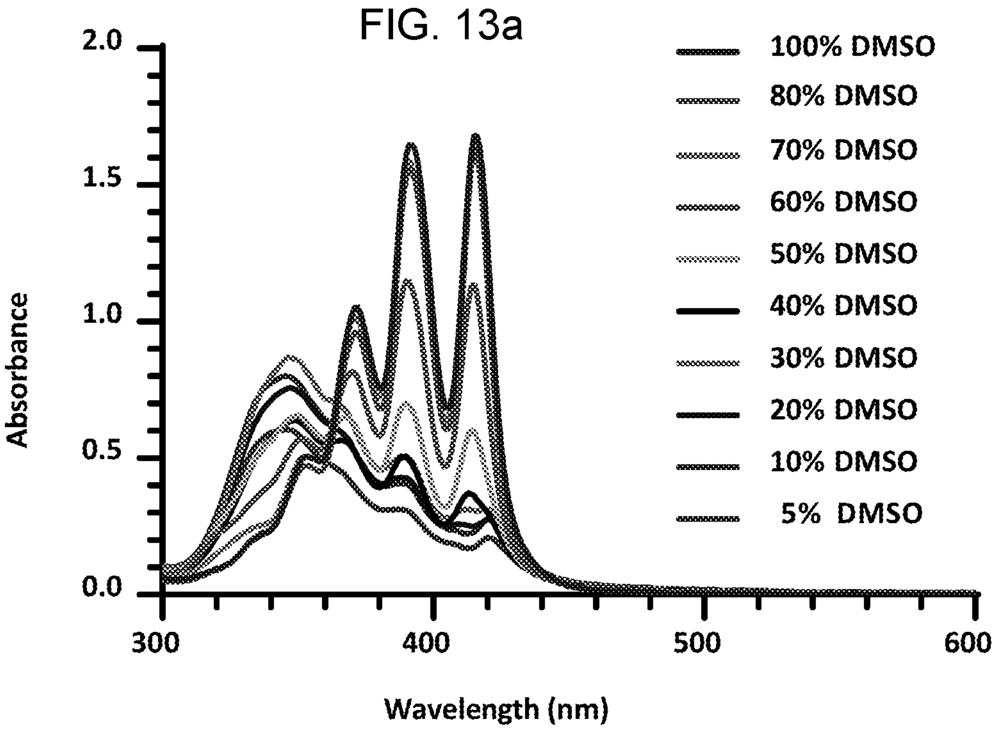
FIG. 13*a* UV-Vis absorption spectra of AmB in different ratio of DMSO/water.
Figure 13B:
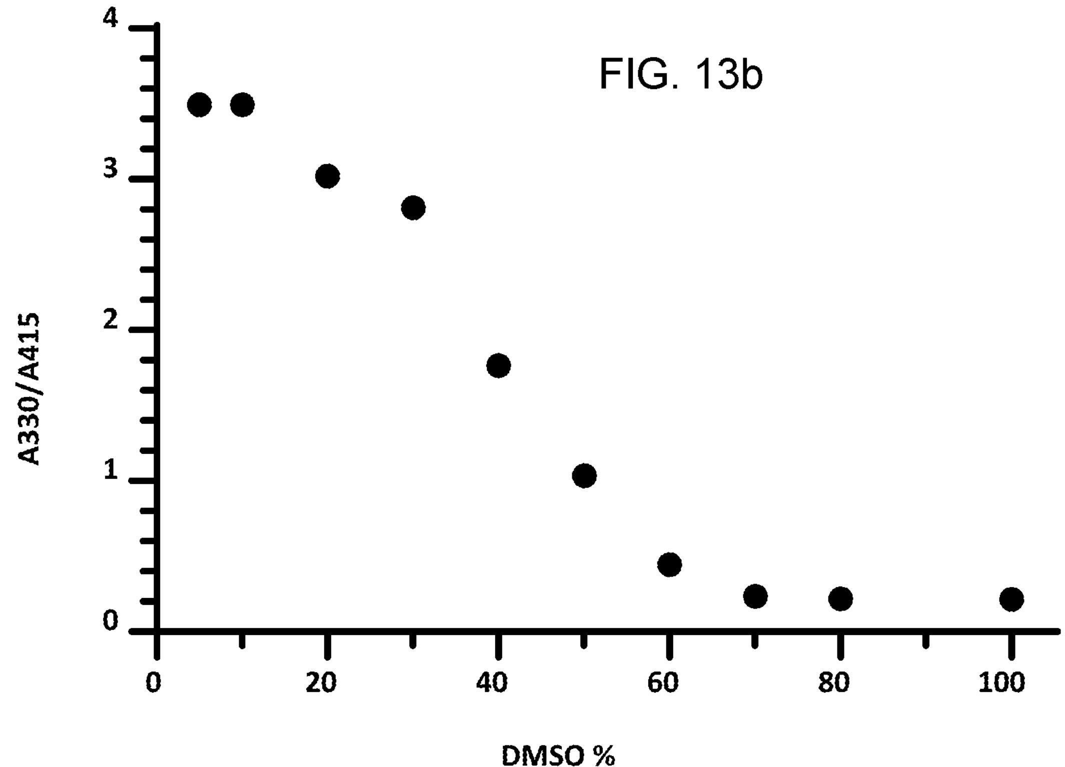
FIG. 13*b* the relationship between A330/A415 ratio of AmB and DMSO/water ratio.

Aggregation status of AmB in nanoformulations: Due to the amphipathic nature, AmB self-associates and aggregates in aqueous solution. The aggregation state of AmB in nanoformulations can be monitored by UV-Vis absorption spectroscopy. In DMSO, AmB presents as soluble monomers and the UV-Vis absorption spectrum is composed of four peaks at around 350, 368, 388 and 415 nm (FIG. 3*a*). However, with the addition of water as a poor solvent, a new peak at around 330 nm appears gradually with increasing water content, indicating aggregation of AmB as shown in FIG. 13. Thus, the ratio of A330/A415 value has been commonly used as the indicator of AmB aggregation status.

Figures 3C, 3D:
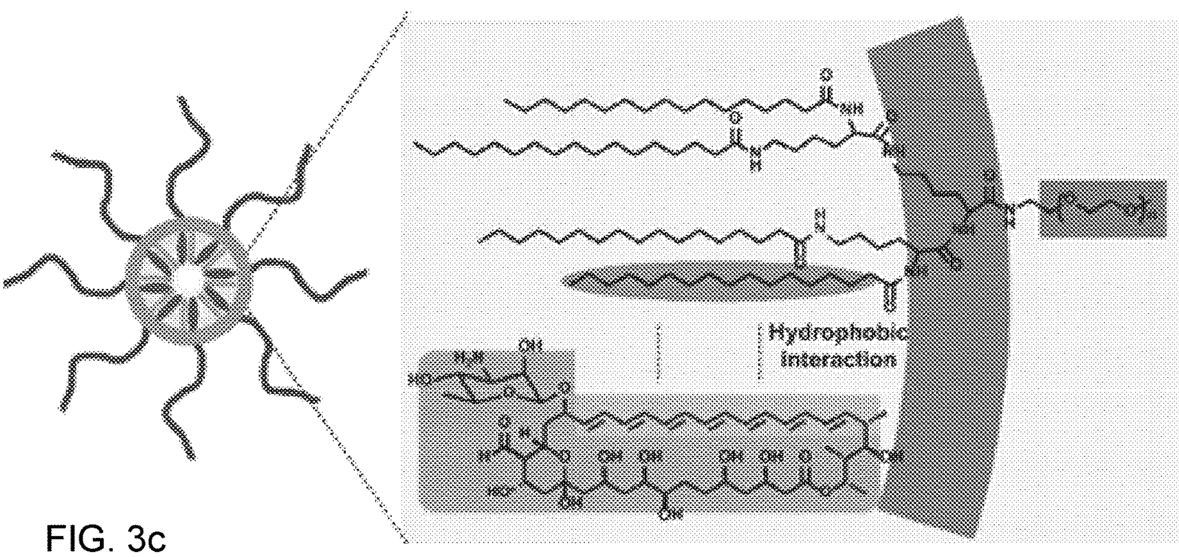
FIG. 3*c* presents a schematic illustration for the hydrophobic interaction between the C17 tail in TD and polyene group in AmB.
FIG. 3*d* presents A330/A415 ratio of free AmB and AmB in nanoformulations calculated based on the UV-Vis absorption spectra.

To determine the aggregation status of AmB in different TD NPs, we recorded the UV-Vis spectra and calculated A330/A415 values of all AmB-TD nanoformulations in comparison with two clinical Fungizone and AmBisome formulations as well as free AmB in DMSO (FIG. 3). The UV-Vis spectra of Fungizone and AmBisome exhibit a sharp band around 330 nm with minor peaks at longer wavelength, and A330/A415 ratios were calculated to be 7.72 and 5.92, respectively, indicating high aggregation status of AmB. As expected, AmB shows different aggregation status after being loaded into TDs with different core structure (FIG. 3*b*) and A330/A415 ratio of AmB ranges from 0.33 to 8.54 in TD NPs (FIG. 3*d*). Interestingly, the $PEG^{5k}C17_4$ at 10/1 mass ratio of TD to drug, showed very low ratio of aggregates to monomer (A330/A415: 0.33) similar to free AmB in DMSO (A330/A415: 0.25) (FIG. 3*a*) without obvious peak observed at 330 nm. This may be due to the flexible C17 fatty acid chain, which effectively interacts with the polyene to separate and stabilize AmB in nanoparticle, thus preventing the self-aggregation of AmB molecules (FIG. 3*c*). As a comparison, we incorporated oleic acid (OA) into TD for AmB encapsulation. OA has a rigid and folded conformation with one cis-double bond at C9 and C10, which reduces the interaction with the rigid polyene in AmB. The AmB-$PEG^{5k}OA_4$ has an increased aggregation state with a A330/A415 ratio of 3.54. Cholesterol (CHO) has a rigid but relatively flat sterol structure, which is known to interact with AmB in mammalian cell membrane. Thus, TD with CHO in the core significantly reduces the aggregation of AmB with an observed A330/A415 ratio of 0.99, due to the favorable AmB interaction. Further, we introduced more rigid bile acids but with the bended sterol ring structures, e.g., cholic acid (CA) and deoxycholic acid (dCA) in TD construction to mimic Fungizone (deoxycholate micelle). As results, AmB adopts high aggregation state in TD micelles containing CA (A330/A415: 8.01) and dCA (A330/A415: 8.54). Interestingly, vitamin E (VE) with a hybrid structure of rigid and flexible fragments significantly reduces the aggregation of AmB with a A330/A415 ratio of 1.19. We also made TD with longer PEG chain $PEG^{20k}C17_4$ to compare with $PEG^{5k}C17_4$ (FIG. 3*b* and FIG. 3*d*). Surprisingly, AmB shows a higher aggregate state (A330/A415: 3.19) in $PEG^{20k}C17_4$ at a TD/AmB mass ratio of 10 to 1. This may be due to the relatively reduced ratio of the C17 to AmB in the NP, which is not sufficient to constrain AmB from aggregation. Accordingly, the increased ratio of $PEG^{20k}C17_4$/AmB to 20/1 and 30/1 significantly reduces AmB aggregation with decreased A330/A415 ratios to 0.83 and 0.44, respectively. All these data indicated that the monomeric AmB in TD nanocarrier can be achieved by introducing flexible lipid molecules or flat molecules for effective AmB interactions.

Figure 4A:
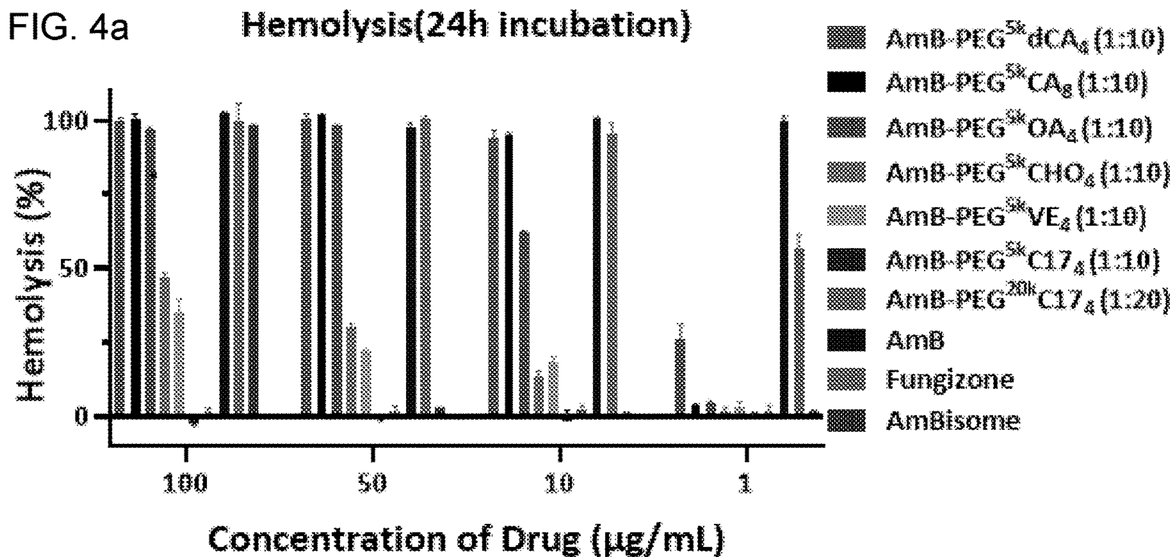
FIG. 4*a* presents In vitro hemolytic activity of AmB and AmB-TDs after incubation with RBCs at different concentrations of AmB for 24 h.
Figure 4B:
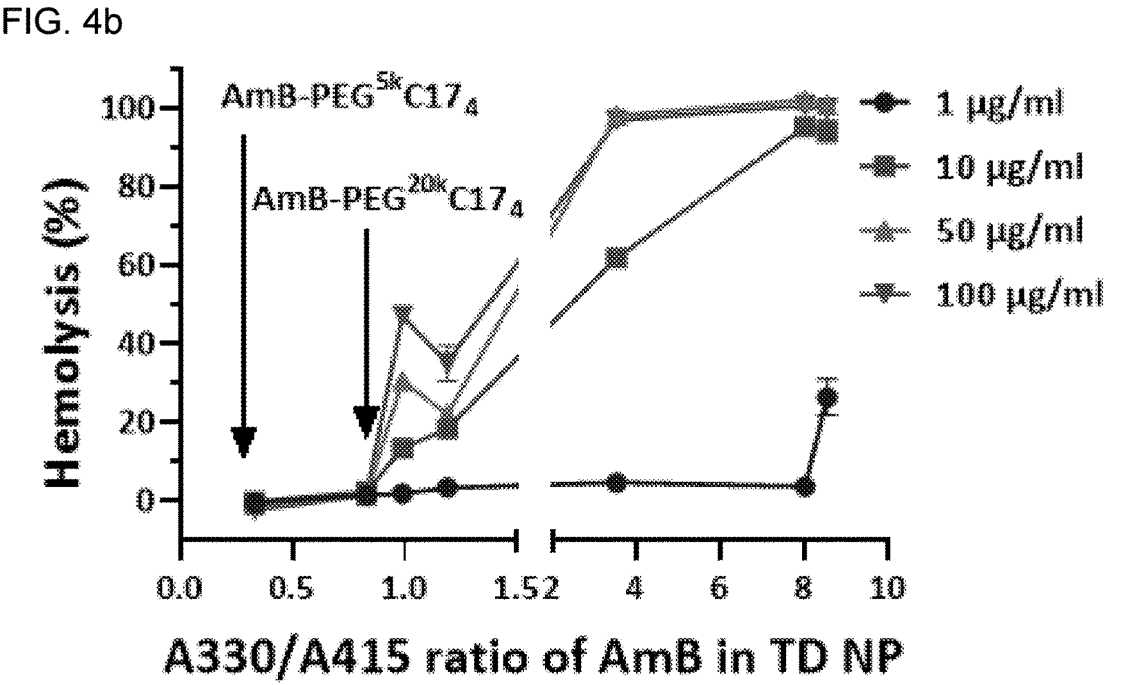
FIG. 4*b* presents the relationship between A330/A415 ratio of AmB in TD NPs and the hemolytic toxicity at different AmB concentrations; agarose gel electrophoresis profiles reveal the release of free doxorubicin from Doxil after incubation with FIG. 4*c* Fungizone and free AmB and FIG. 4*d* AmBisome, AmB-$PEG^{5k}C17_4$, AmB-$PEG^{5k}dCA_4$ (1:10 mass ratio of AmB to TD) at an equivalent AmB concentration of 100 µg/mL for 24 h at 37° C.
Figure 14:
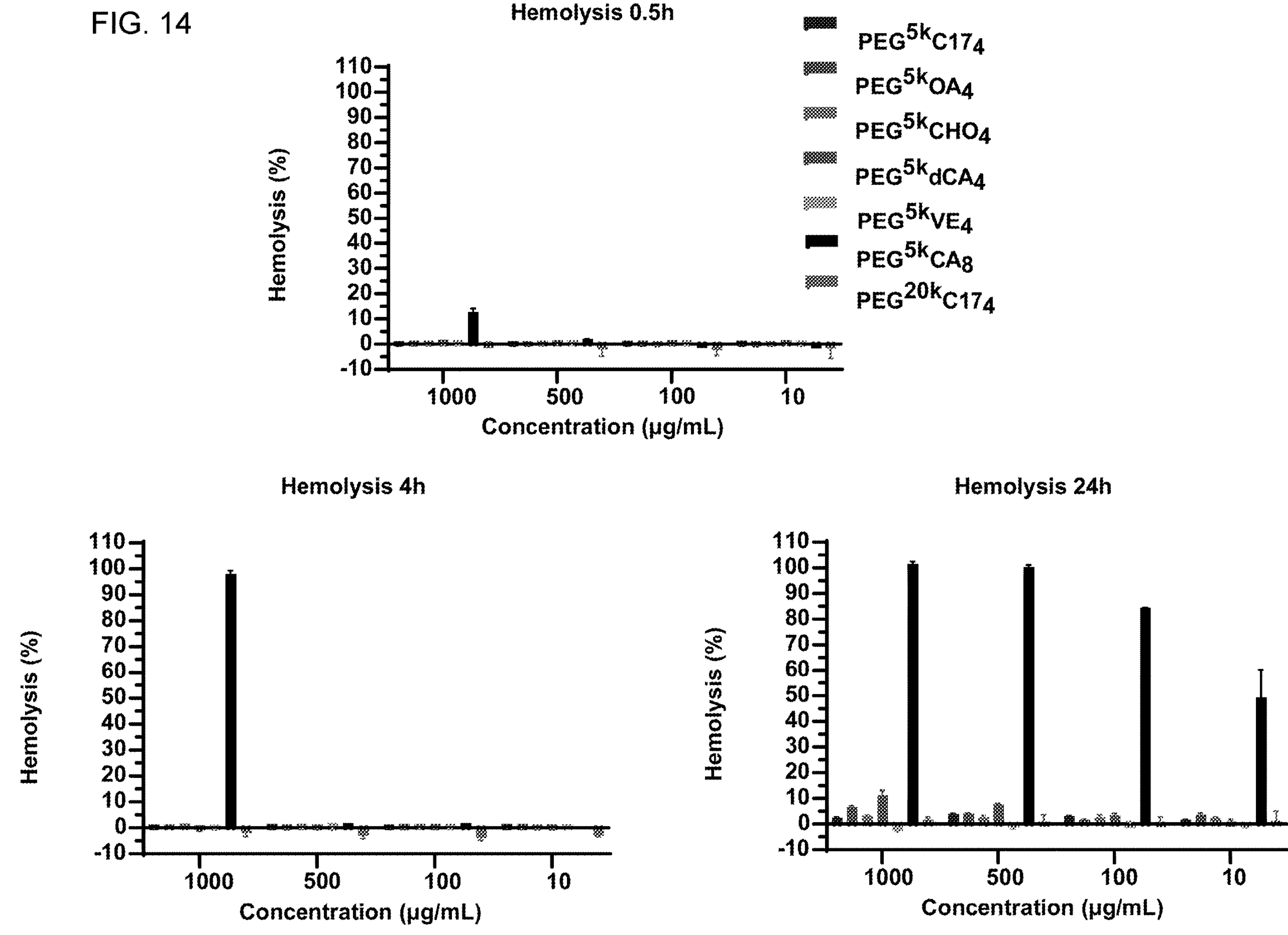
FIG. 14. In vitro hemolytic activity of TDs after incubation with red blood cells at different concentrations for 0.5, 4 h and 24 h.
Figure 15:
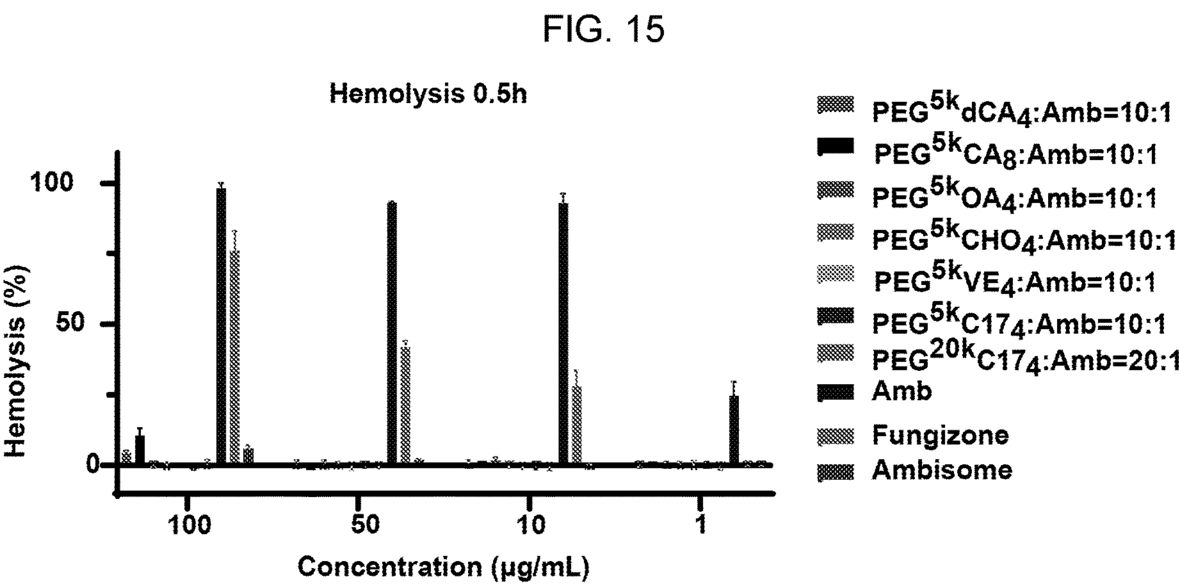
FIG. 15. In vitro hemolytic activity of AmB-TDs after incubation with red blood cells at different concentrations of AmB for 0.5 and 4 h.
Figure 15:
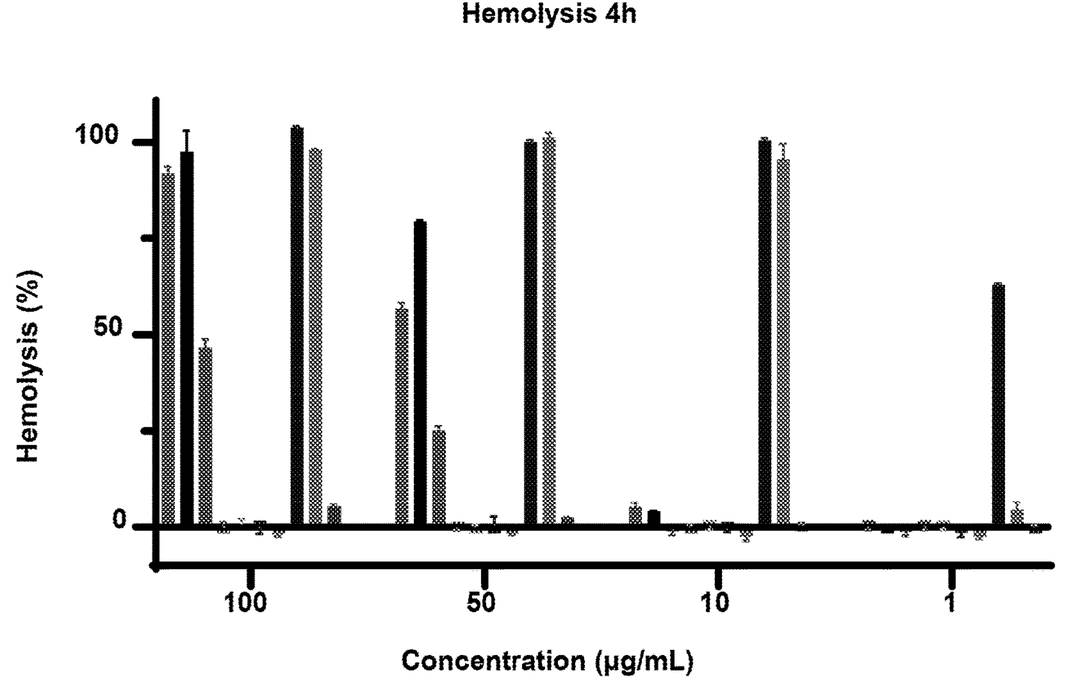

Cytotoxicity and hemolysis of AmB-TD nanoformulations: Binding of AmB with cholesterol in erythrocytes/RBC membrane and consequent haemolysis is a major toxicity concern of AmB. The drug aggregation state is a key element for hemolytic activity. Most of the TDs are safe for hemolysis except for TD with CAs showing mild hemolytic activity (~12%) at high concentration (1 mg/mL) after 30 min incubation due to the membrane activity of cholic acid (FIG. 14). Significant hemolysis (~25%) was observed for free AmB incubation with concentration at 1 μg/mL for 30 min (FIG. S7), which reaches to 100% after 24 h incubation (FIG. 4*a*). AmBisome and Fungizone were used at the equivalent concentrations of AmB for comparison. The Fungizone shows a similar hemolysis as the free drug, due to the high aggregation state (FIG. 3*a*) and fast drug release profile (FIG. 2*g*). AmBisome exhibits much less hemolysis although with high AmB aggregation observed. However, it still shows 100% hemolysis after 24 h incubation at 100 μg AmB/mL, owing to the aggregated state of AmB (FIG. 3*a*). In comparison, TDs with C17 ($PEG^{5k}C17_4$ and $PEG^{20k}C17_4$) with the lowest ratio of AmB aggregation are non-haemolytic even at a drug concentration of 100 μg/mL after 24 h incubation (FIG. 4*a*). It is much safer than other similar PEGylated lipid micelle systems reported in the literature, e.g. DSPE-PEG, which exhibited mild haemolytic properties only at lower drug concentration of 10-50 μg/mL for short time incubation (0.5-1 h). It may be due to the flexible dendritic tetravalent fatty acid chains in TD, which provides more effective interactions with AmB to prevent aggregation formation and stabilize the drug encapsulation. TDs with dCA, CA and OA with higher aggregation state reveal significant haemolytic activity with the increased concentrations. In comparison, TDs with CHO and VE with relatively low ratio of AmB aggregation, only show moderate haemolysis toxicity at the highest tested drug concentration of 100 μg/mL after 24 h incubation (FIG. 4A and FIG. 15). In order to elucidate the correlation of the haemolytic property with the AmB aggregation status, we plot haemolysis against A330/A415 ratio of AmB in TD NPs at different concentration after 24 h incubation as shown in FIG. 4*b*. Strong correlations between AmB aggregation status and haemolysis were observed at all concentrations. Both concentration dependency and aggregation dependency were observed in hemolytic plot (FIG. 4B) and only C17-containing nanoformulations with A330/A415 less than 1 revealed non-haemolytic properties at all tested concentrations.

Figure 4C:
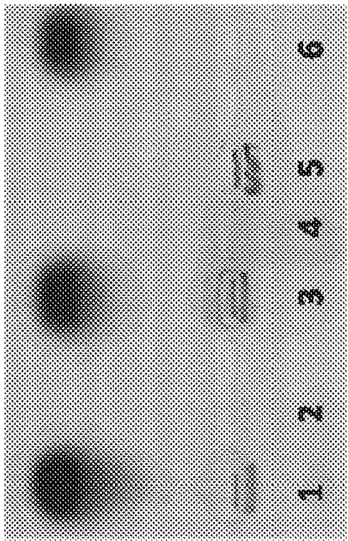
FIG. 4*e* presents dose-dependent release of free doxorubicin from Doxil after incubation with different AmBisome to Doxil ratio demonstrated by agarose gel electrophoresis.
Figure 4D:
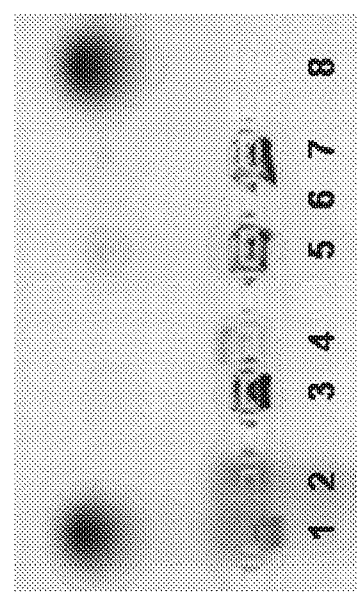
Figure 4E:
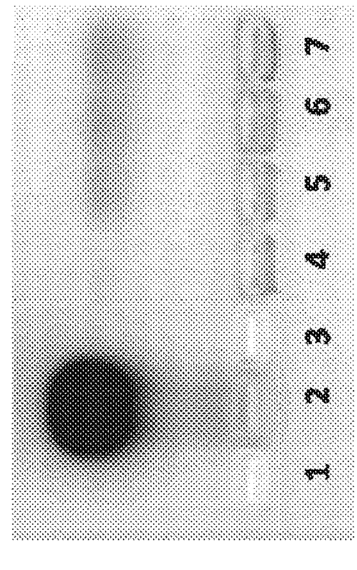
Figure 4E:
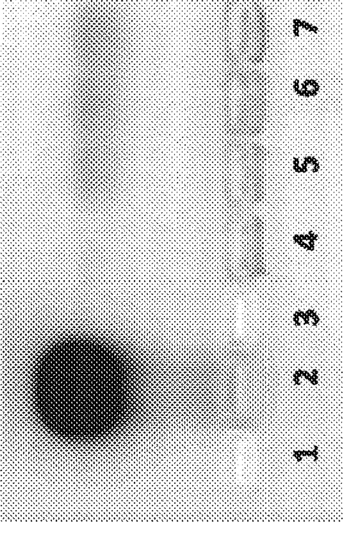

In order to further evaluate the membrane activity, we applied liposomal doxorubicin (DOX) nanoformulation (Doxil) as a model vesicle to probe the erythrocyte leakage by AmB-TDs. The leakage of fluorescent DOX from Doxil can be easily monitored by electrophoresis, where free DOX migrates along with the electric field, but Doxil will be trapped in the loading well due to the large particle sizes (80-100 nm) and neutral charges (FIG. 4*c*-FIG. 4*e*). As shown in FIG. 4*c*, Fungizone and free AmB with high AmB aggregation status in aqueous solution result in significant DOX release from Doxil, which are consistent with their strong hemolysis activity (FIG. 4*a* and FIG. 4*b*). Similarly, AmB-$PEG^{5k}dCA_4$ also causes significant DOX leakage from Doxil (FIG. 4*d*). In contrast, the monomeric AmB in $PEG^{5k}C17_4$ nanoparticle barely causes noticeable DOX release in comparison with Doxil only. Interestingly, AmBisome only causes small amount DOX release, despite of its high AmB aggregation status. It may be mainly due to the slow-release profile. However, with increasing concentration of AmBisome, noticeable dose-dependent DOX leakage was observed in FIG. 4*e*, which correlates to its haemolytic properties at high concentration (FIG. 4*a*). In summary, both hemolytic assay and Doxil leakage assay indicate that the monomeric AmB nanoformulations are non-haemolytic for safe in vivo application.

Figure 5A:
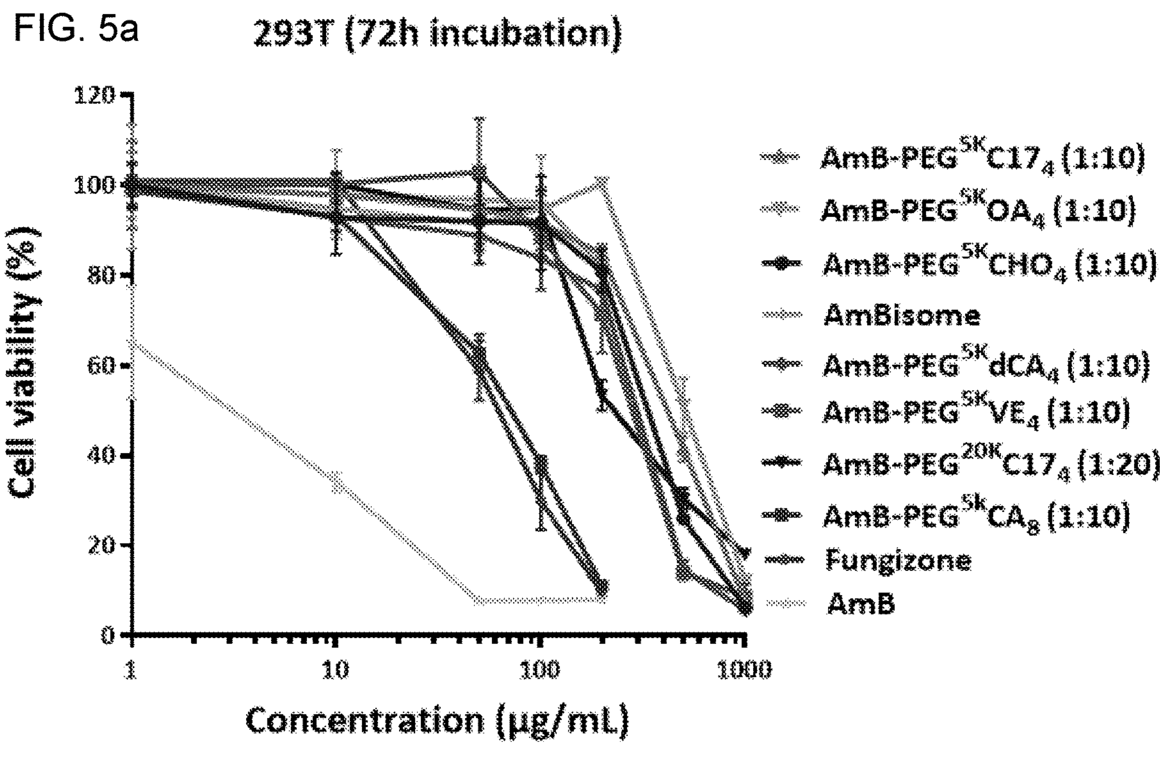
FIG. 5*a* presents In vitro cell viability of 293T cells and FIG. 5*b* RAW 264.7 after 72 h incubation with free AmB and AmB-nanoformulations at different concentrations of AmB (mean±SD, n=3)
Figure 5B:
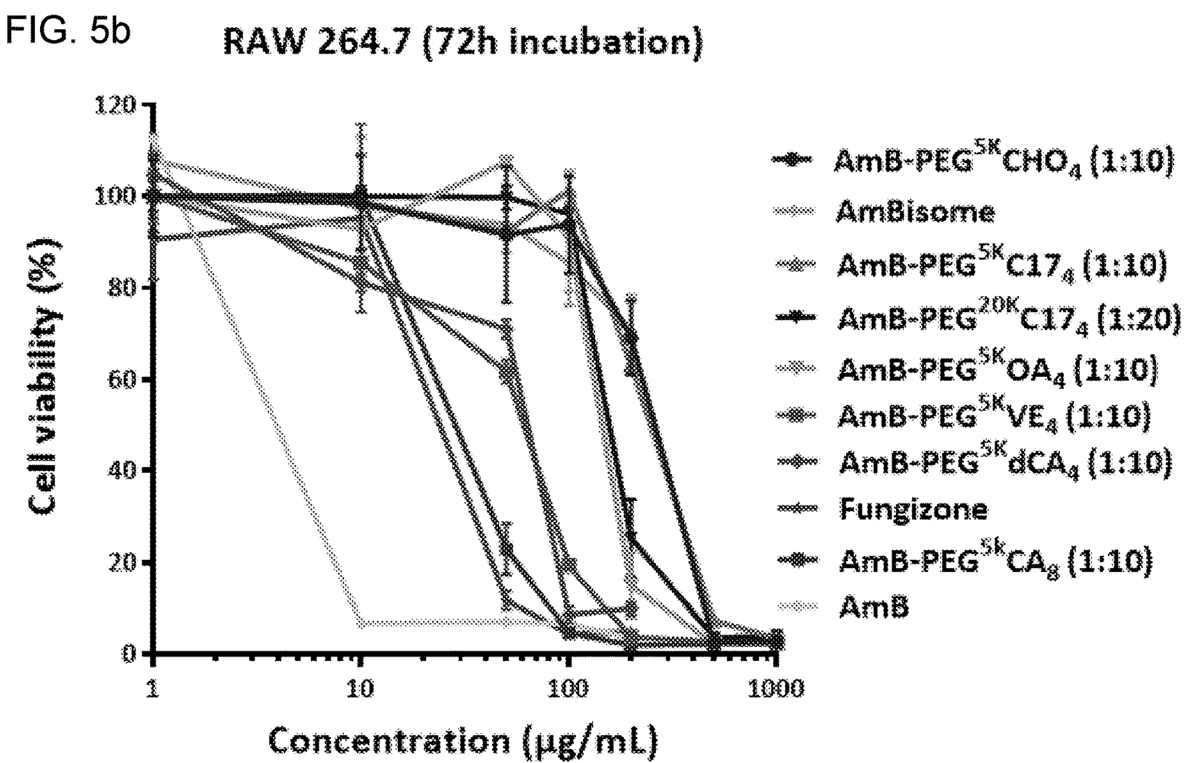
FIG. 5*c* presents in vitro antifungal activity MIC (minimum inhibition concentration, µg/mL) of free AmB and various AmB formulations against *C. albicans* in cell culture; and the cytotoxicity of free AmB and various AmB formulations in cell culture with kidney cells 293T and murine macrophage cells RAW 264.7 as presented as IC50 (50% inhibition concentration, µg/mL); Further, the in vitro therapeutic index of nanoformulations were calculated as IC50/MIC for both cell lines.
Figure 16:
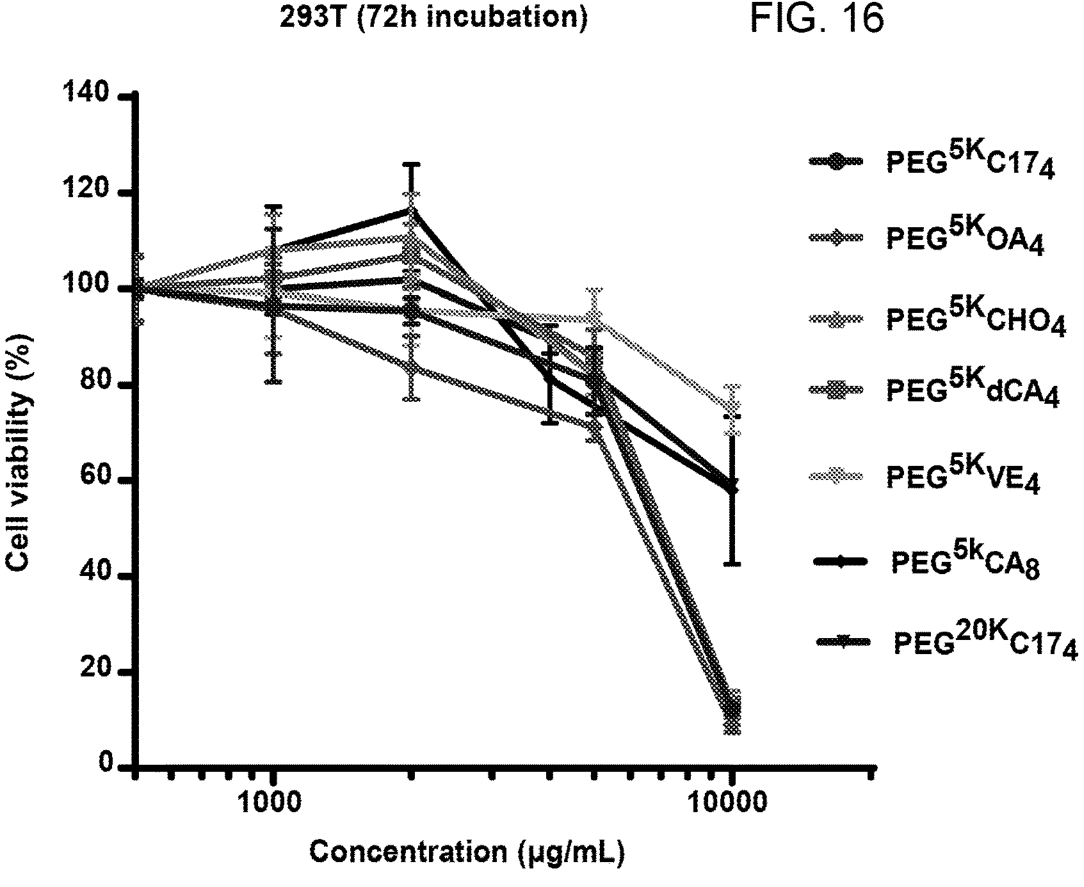
FIG. 16. In vitro cell viability of 293T and RAW 264.7 cells after 72 h incubation with TDs at different concentrations.
Figure 16:
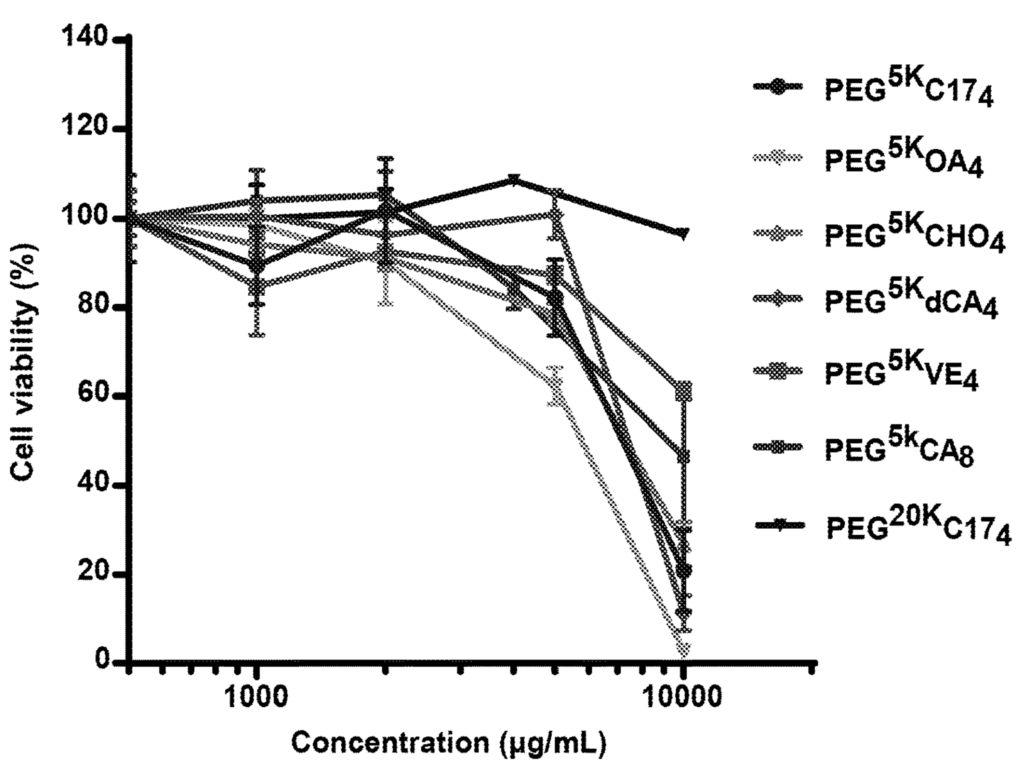
Figure 17:
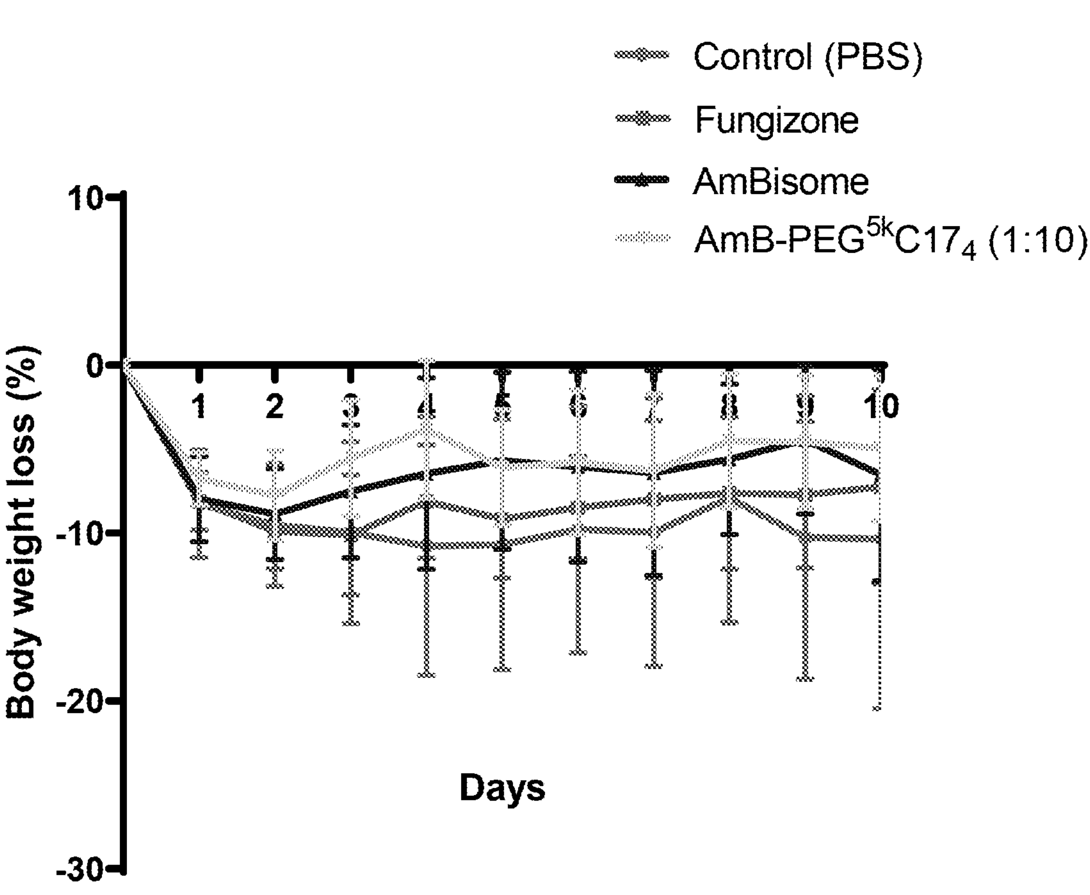
FIG. 17. The body weight changes of mice infected with *C. albicans* and treated either with Fungizone, AmBisome and AmB-$PEG^{5k}C17_4$ at 1 mg AmB/kg compared to untreated controls.
Figure 18:
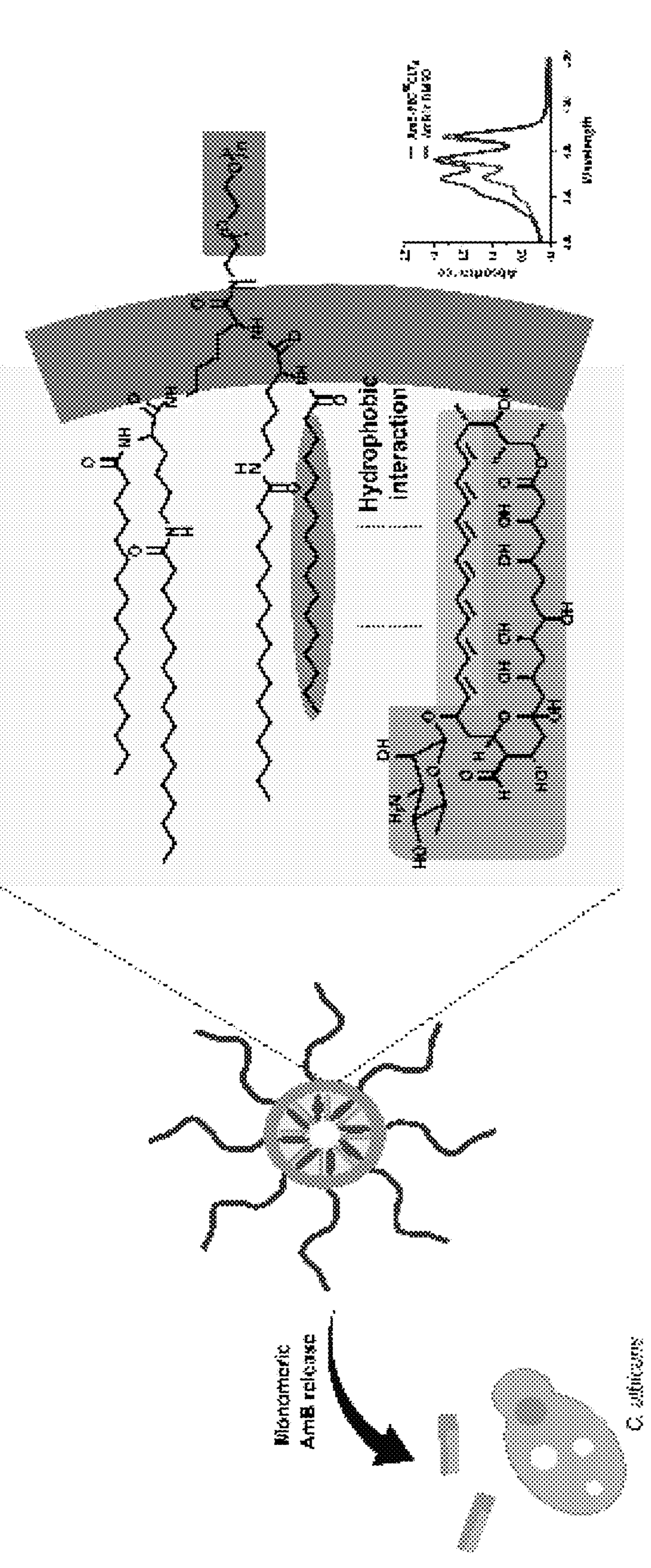
FIG. 18 presents a schematic illustration for the hydrophobic interaction between the C17 tail in TD and polyene group in AmB, and the release of monomeric AmB from the TD micelles for the therapeutic destruction of *C. albicans.*

Besides erythrocytes, the membrane activity of AmB may also result in cytotoxicity to tissue and immune cells, e.g., kidney cell and macrophages, particularly macrophages because of their role in nanoparticle clearance. Thus, we evaluated the cytotoxicity of AmB nanoformulations in cell culture with 293T kidney cell line and RAW 264.7 murine macrophage cells (FIG. 5*a* and FIG. 5*b*). The empty TDs exhibit good biocompatibility with no obvious cytotoxicity up to 4 mg/ml (FIG. 16). Compared to the free AmB (IC50: 4.3 μg/mL to 293T, 1.8 μg/mL to RAW 264.7), all AmB nanoformulations, including Fungizone, show reduced cytotoxicity in both cell cultures. Fungizone showed significantly higher cytotoxicity, with IC50 60 μg/mL to 293T cells and 41 μg/mL to RAW cells (FIG. 5*c*). AmB-TD formulation with CA groups show similar IC50 with Fungizone, due to both high aggregation state of AmB and high membrane activity of TD (CA) nanocarrier. The rest nanoformulations show significantly improved biocompatibility in kidney cells without cytotoxicity observed at or above 100 μg/mL AmB concentration. In RAW cell culture, AmB nanoformulations with lower aggregation state generally have better biocompatibility in cell culture. For example, AmB-TD formulations with C17 and CHO as building blocks (A330/A415 ratios: 0.33 and 0.99) show better biocompatibility with IC50s above 200 μg/mL similar to the liposomal formulation AmBisome (IC50: 215 μg/mL) after 72 h incubation (FIG. 5*c*). These results clearly indicate that efficient monomeric AmB encapsulation in optimized TD NPs can effectively decrease the cytotoxicity. It is interesting to observe that AmB nanoformulations are more tolerable in kidney cells than red blood cells and macrophages (FIG. 4*a* and FIG. 5*c*). It may be due to the higher cholesterol content on human erythrocytes membrane, about 1-1.5 times richer than other cells in human body, which provide stronger AmB binding affinity for membrane lysis.

In vitro antifungal activity of AmB nanoformulations: Nanoparticle encapsulation may impact drug efficacy due to the drug availability for action. We performed in vitro culture of typical pathogenic fungus *C. albicans* (ATCC 10231) in the presence of AmB formulations at different concentration to determine the minimum inhibitory concentration (MIC). A suspension of fungi ($5\times10^6$ cells/mL) was incubated with different concentrations of AmB-TDs for 24 h at 25° C. The free AmB, as well as AmBisome and Fungizone with equivalent concentration of drug were included as controls, and the results are summarized in FIG. 5*c*. MIC of free drug was determined to be 0.05 μg/mL, while the activity of AmBisome and Fungizone were less effective with MICs determined to be 0.2 and 0.1 μg/mL, respectively, due to slow release. Most of AmB-TD nanoformulations exhibits the same MIC for antifungal efficacy against *C. albicans* as the free AmB at 0.05 μg/mL. The empty TD nanocarriers have no antifungal activity in inhibiting *C. albicans* growth. However, AmB-PEG$^{5k}$C17$_4$ with the reduced cytotoxicity even shows more potency with a MIC two-times lower than Fungizone and 4-times lower than AmBisome. The small particle sizes and the release of more effective monomeric AmB may explain the higher antifungal activity and reduced cytotoxicity over host cells. In order to evaluate the therapeutic index of AmB formulations, we took the ratio of IC50 for host cells over MIC concentrations as shown in FIG. 5*c*. AmB-PEG$^{5k}$C17$_4$ shows the highest therapeutic index with IC50/MIC as high as 4100 (RAW 264.7 cells), which is much higher than AmBisome (1075). In contrast, the therapeutic index of Fungizone and free AmB were determined to be 410 and 36, respectively. Based on the therapeutic index to both cell lines, AmB-PEG$^{5k}$C17$_4$ was determined to have the best safety profile, thus was carried forward for in vivo studies.

Pharmacokinetics and acute in vivo toxicity: Fungizone and AmBisome are commonly administrated in the clinic through intravenous infusion to treat systemic and deep tissue fungal infections. Thus, the pharmacokinetics of AmB-PEG$^{5k}$C17$_4$ formation was characterized in comparison with both Fungizone and AmBisome in normal mice. AmB-PEG$^{5k}$C17$_4$ was intravenously injected in mice at a dose of 1 mg AmB/kg by referencing Fungizone dosage in the literature. The blood concentration of AmB were evaluated by UV-Vis spectrometry (415 nm) after extraction. Fungizone and AmBisome were used at the same dose level for comparison. The plasma concentrations over time were plotted in FIG. 6*a*, the pharmacokinetic parameters were shown in Table S1. The AmB concentration of Fungizone declined fast even at the first time point of sampling at 5 min post-injection and became undetectable in the plasma of mice 12 h after injection. However, TD nanoformulation showed more sustained drug concentration in blood similar to AmBisome. AmB-PEG$^{5k}$C17$_4$ showed over 3-fold higher of area under curve (AUC) (58.6±12.66 mg·h/L) of PK profile and longer half-life ($T_{1/2}$, 1.64 h) in comparison with that of Fungizone (AUC 18.33±2.09 mg·h/L, $T_{1/2}$ 0.05 h). It is known that the liposome formulations have better in vivo stability and long circulation time. Our AmB-PEG$^{5k}$C17$_4$ nanoformulation exhibits a similar PK profile with AmBisome (AUC 72.06±12.62 mg·h/L, $T_{1/2}$ 2.59 h), suggesting for effective antifungal therapy in vivo.

TABLE S1

Pharmacokinetic parameter of AmB in plasma for AmB-PEG$^{5k}$C17$_4$ and clinical products (AmBisome and Fungizone).

| Parameters | Fungizone | AmBisome | AmB-PEG$^{5k}$C17$_4$ (1:10 mass ratio) |
|---|---|---|---|
| $T_{1/2}$ (h) | 0.046 | 2.590 | 1.644 |
| AUC (mg · h/L) | 18.33 | 72.06 | 58.6 |
| $C_{max}$ (μg/mL) | 7.23 | 16.75 | 21.39 |
| CL (mL/kg/h) | 40.15 | 0.38 | 0.44 |
| $V_{ss}$ (mL/kg) | 111.33 | 1.31 | 1.47 |

$T_{1/2}$ (h): half-life; AUC (mg · h/L): area under the concentration time curve; $C_{max}$ (μg/mL): the maximum observed concentration at the earliest evaluated time point of 5 min post i.v. injection; CL (mg/mL): apparent total clearance of the AmB from plasma; $V_{ss}$ (mL/kg): steady-state volume of distribution.

Figures 6A, 6B:
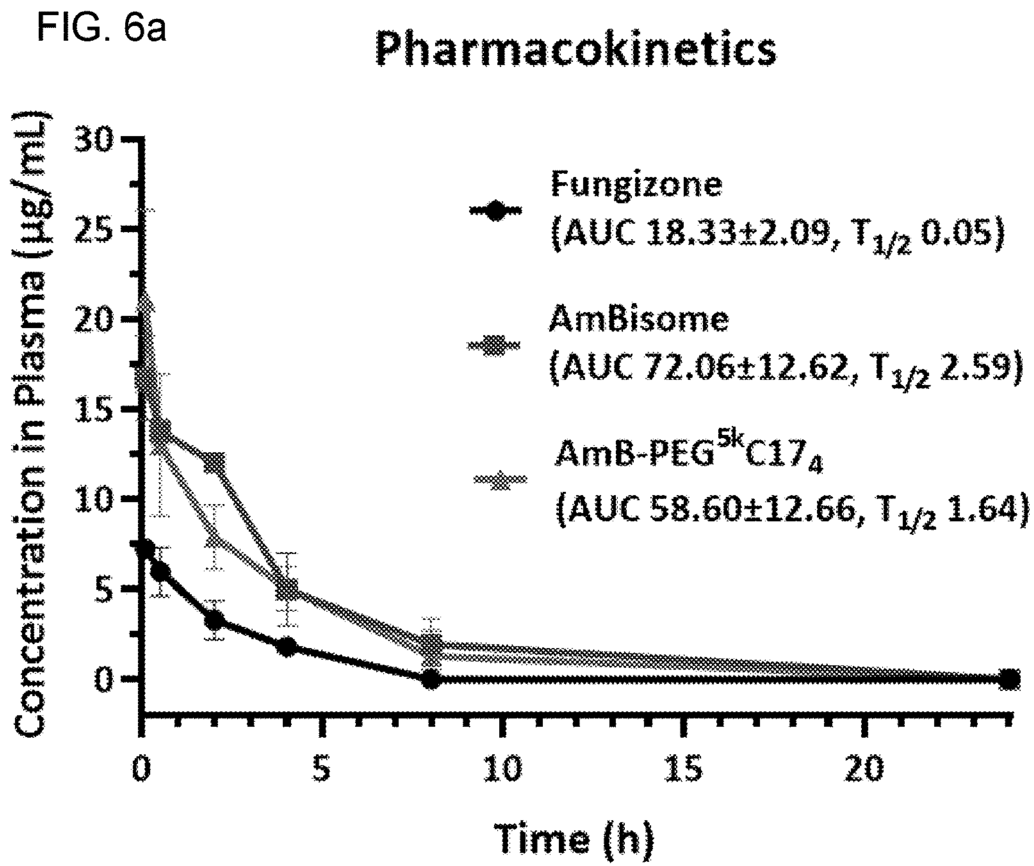
FIG. 6*a* presents the plasma concentration-time profile of AmB-$PEG^{5k}C17_4$ (1:10) and clinical products (AmBisome and Fungizone) after administration as a single dose of 1 mg/kg i.v. injection. AUC (mg·h/L): area under the concentration time curve; $T_{1/2}$ (h): half-life; data are expressed as the mean±SD (n=3-4)
FIG. 6*b* presents the survival of mice after a single dose of AmB-NPs by i.v. injection at AmB dose of 2 mg/kg (n=3-4).

Fungizone is known to be associated with both infusion reaction and severe renal toxicity, which is called "Amphoterrible" in the clinic. In animal studies, Fungizone is also associated with low and narrow dose window as of <1 mg/kg. To evaluate the safety profile of AmB-TD nanoformulations with different aggregation status, we conduct an in vivo toxicity study in normal mice by i.v. injection of drug formulations in comparison to Fungizone and AmBisome at 2 mg/kg dose level to monitor acute mortality caused by infusion reactions. As shown in FIG. 6*b*, Fungizone is very toxic in mice with only 33% survival after injection. As expected, AmBisome is very safe and yields a 100% survival at same dosage. Surprisingly, some AmB-TD nanoformulations led to significant high mortality. For example, in AmB-PEG$^{5k}$dCA$_4$ and AmB-PEG$^{5k}$VE$_4$ groups, all mice died after i.v. injection; AmB-PEG$^{5k}$CHO$_4$, AmB-PEG$^{20k}$C17$_4$ (1:20 mass ratio) and AmB-PEG$^{5k}$OA$_4$ formulations yield better survival of 33%, 67%, and 75%, respectively, which are comparable or better than Fungizone. Most importantly, the optimal AmB-PEG$^{5k}$C17$_4$ with monomeric AmB status didn't show severe infusion reactions with 100% survival after injection, which is comparable to AmBisome in mice.

Figure 7A:
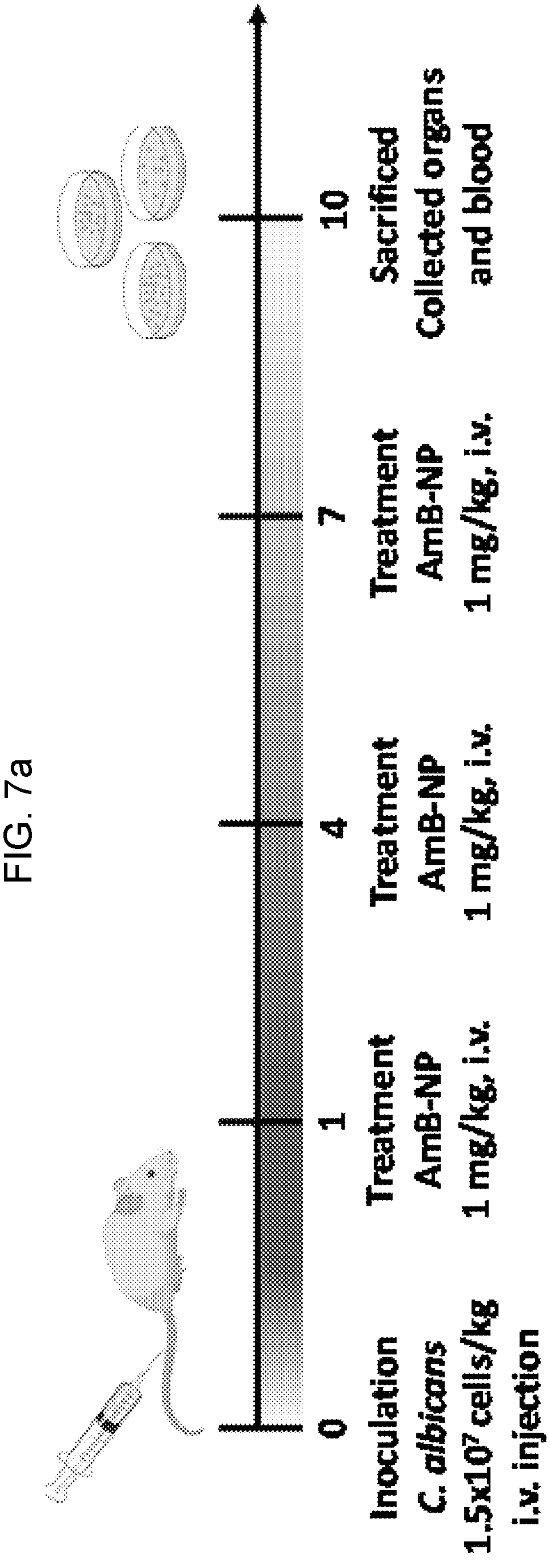
FIG. 7*a* presents a schematic illustration of *C. albicans*-infected mice treatment with AmB-NPs.
Figure 7B:
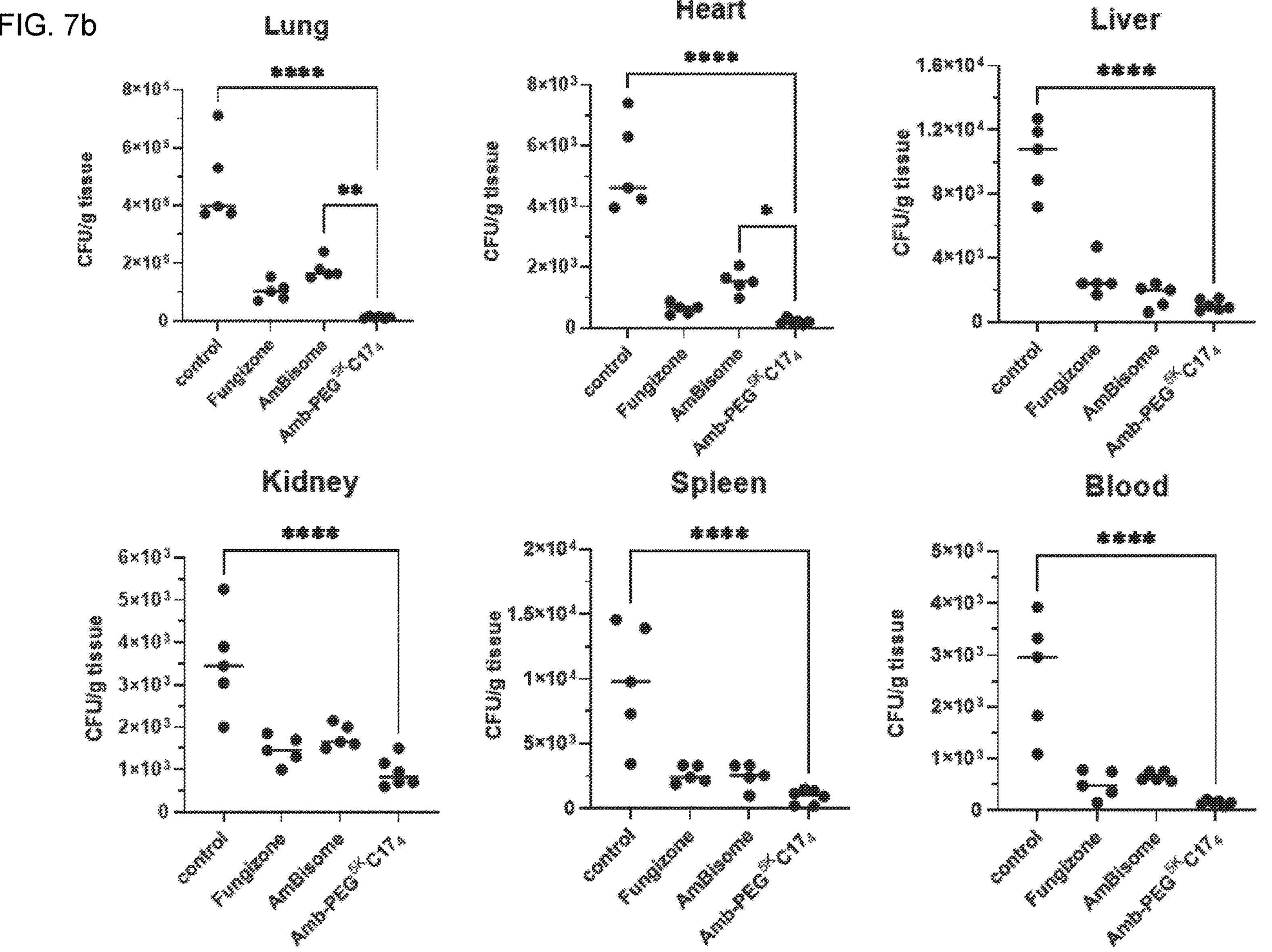
FIG. 7*b* presents fungal burden of lung, heart, liver, kidney, spleen and blood of mice infected with *C. albicans* and treated either with Fungizone, AmBisome and AmB-$PEG^{5k}C17_4$ (1:10) at 1 mg/kg body weight compared to untreated controls. (*: p<0.05; : p<0.01; *: p<0.001; ****: p<0.0001).

In vivo antifungal activity of AmB nanoformulation: Given the superior safety profile, in vitro antifungal effects and improved PK profile of AmB-PEG$^{5k}$C17$_4$ nanoformulation, we continue to evaluate the in vivo antifungal effects in wild type B6 mice with systemic *C. albicans* infection. In order to compare with Fungizone and AmBisome, the dose was set at the same level of 1 mg/kg at Fungizone's tolerable therapeutic dose. As shown in FIG. 7*a, C. albicans* were i.v. injected into mice 24 h before the drug treatments for 3 doses on day 1, 4 and 7. The body weight of mice were monitored daily. The PBS treatment group show more body weight loss, whereas the AmB-PEG$^{5k}$C17$_4$ treatment group show the least body weight loss than Fungizone and AmBisome treatments (FIG. S9). On day 10, all mice were sacrificed, organs and blood were collected for fungi burden analysis as shown in FIG. 7*b*. Significant colony forming units (CFU) reduction in major organs and blood were observed in all three treatment groups than control group. At low dose therapy, AmBisome treatment is slightly less effective than Fungizone in CFU counts. In comparison, AmB-TD treatment showed the most effective antifungal effects among three groups, evidenced by the significantly low CFU count than AmBisome in lung and heart.

Figure 8:
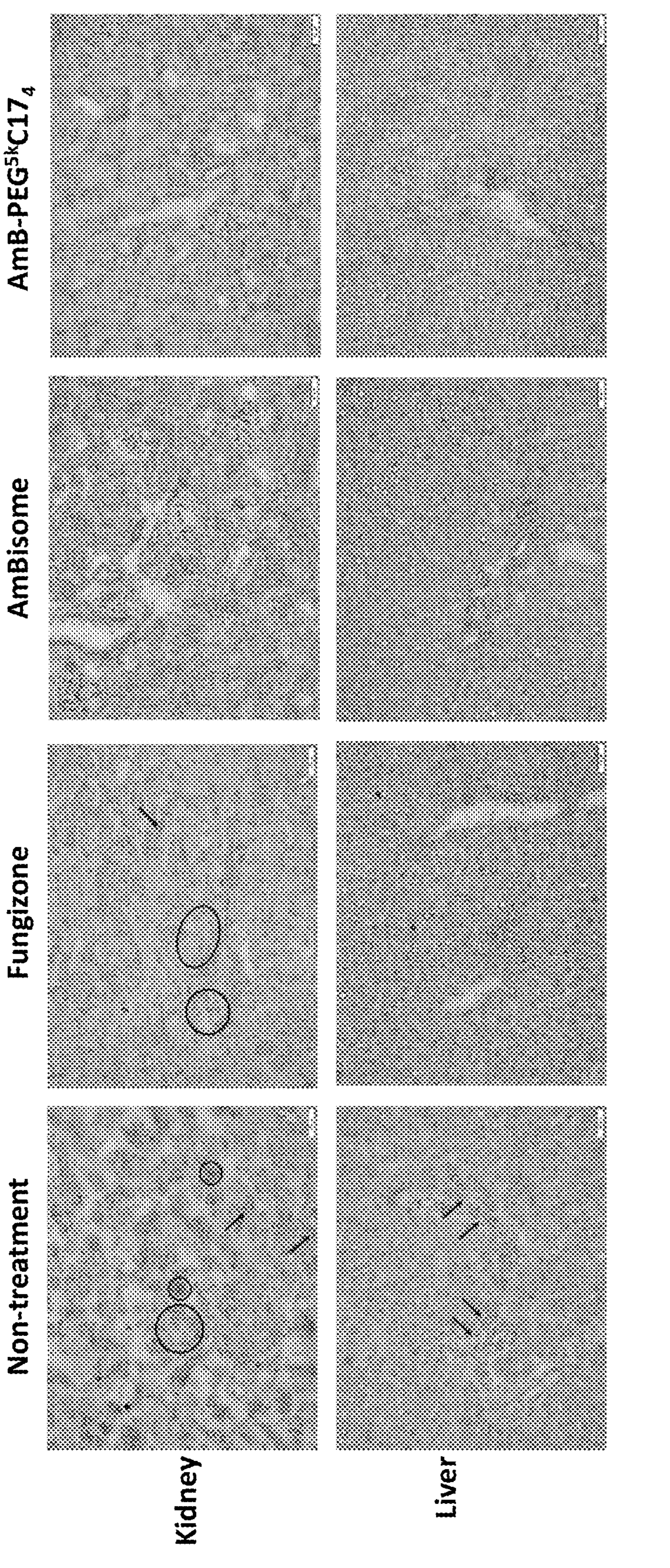
FIG. 8 presents renal and liver histology (stained with H & E) of *C. albicans* infected mice treated by PBS, Fungizone, AmBisome and AmB-$PEG^{5k}C17_4$. Black circle: glomeruli; blue circle: tubular necrosis; blue arrows: inflammation. Scale bar: 50 µm.

It is known that animals with competent immunity can effectively control fungal infections at certain level. In this study, fungal challenging at $1.5\times10^7$ cells/kg *C. albicans* indeed causes significant threat to animal health as demonstrated by body weight changes and organ fungal load. Further, organ histology studies by H&E staining revealed significant tissue damage and inflammation in kidney and liver, but not significant for other organs. As shown in FIG. 8, the kidney of the non-treated mice showed diffused tubular necrosis with marked interstitial inflammation. The kidneys of groups treated with AmBisome and AmB-PEG$^{5k}$C17$_4$ showed normal-appearing histologic structures with rare tubular injury or inflammation. However, acute tubular epithelial injury with necrosis was observed in Fungizone-treated mice, although the interstitial inflammation was decreased compared with non-treated group. As for the liver, a significant higher population of infiltrating inflammatory cells around the bile duct of portal triad as well as liver parenchyma were found in non-treated mice. Livers in animals treated by all the other three AmB nanoformulations depicted quite normal morphology without significant infiltration of inflammatory cells.

Embodiments disclosed herein demonstrated a precise control of AmB aggregation status in TD nanocarriers by engineering TD structures to fine-tune AmB-nanocarrier interaction. The nanoformulations with monomeric AmB status significantly reduce the haemolytic properties and improved the cytotoxicity to host cells, while maintaining antifungal activity, thus improve therapeutic windows compared with the clinical AmB formulations, i.e., Fungizone and AmBisome. The optimized TD nanoformulation AmB-PEG$^{5k}$C17$_4$ improves the PK profile and reduces in vivo toxicity of AmB to a level that are similar to AmBisome, but much improved than Fungizone. In vivo antifungal studies revealed even improved efficacy of AmB-PEG$^{5k}$C17$_4$ than both Fungizone and AmBisome, due to both improved safety and antifungal activity. In addition, TD nanocarrier can be precisely synthesized in large scale at low cost, which promises a more effective and low-cost AmB formulation for clinical translation in treating lethal fungal infections.

REFERENCES: (1) Gray, K. C.; Palacios, D. S.; Dailey, I.; Endo, M. M.; Uno, B. E.; Wilcock, B. C.; Burke, M. D. Amphotericin primarily kills yeast by simply binding ergosterol. *Proceedings of the National Academy of Sciences* 2012, 109 (7), 2234-2239. (2) De Kruijff, B.; Demel, R. A. Polyene antibiotic-sterol interactions in membranes of Acholeplasma laidlawii cells and lecithin liposomes. III. Molecular structure of the polyene antibiotic-cholesterol complexes. *Biochimica et Biophysica Acta* (BBA)—Biomembranes 1974, 339 (1), 57-70. DOI: doi.org/10.1016/0005-2736 (74) 90332-0. (3) Umegawa, Y.; Yamamoto, T.; Dixit, M.; Funahashi, K.; Seo, S.; Nakagawa, Y.; Suzuki, T.; Matsuoka, S.; Tsuchikawa, H.; Hanashima, S.; et al. Amphotericin B assembles into seven-molecule ion channels: An NMR and molecular dynamics study. *Science Advances* 2022, 8 (24), eabo2658. DOI: doi: 10.1126/sciadv.abo2658. (4) Laniado-Laborín, R.; Cabrales-Vargas, M. N. Amphotericin B: side effects and toxicity. *Revista iberoamericana de micología* 2009, 26 (4), 223-227. Volmer, A. A.; Szpilman, A. M.; Carreira, E. M. Synthesis and biological evaluation of amphotericin B derivatives. *Natural product reports* 2010, 27 (9), 1329-1349. (5) Diezi, T. A.; Kwon, G. Amphotericin B/sterol co-loaded PEG-phospholipid micelles: effects of sterols on aggregation state and hemolytic activity of amphotericin B. *Pharmaceutical research* 2012, 29 (7), 1737-1744. (6) Espada, R.; Valdespina, S.; Alfonso, C.; Rivas, G.; Ballesteros, M. P.; Torrado, J. J. Effect of aggregation state on the toxicity of different amphotericin B preparations. *International Journal of Pharmaceutics* 2008, 361 (1), 64-69. DOI: doi.org/10.1016/j.ijpharm.2008.05.013. Adams, M. L.; Kwon, G. S. Relative aggregation state and hemolytic activity of amphotericin B encapsulated by poly(ethylene oxide)-block-poly(N-hexyl-L-aspartamide)-acyl conjugate micelles: effects of acyl chain length. *J Control Release* 2003, 87 (1-3), 23-32. DOI: 10.1016/s0168- 3659 (02) 00347-4 From NLM. Legrand, P.; Romero, E. A.; Cohen, B. E.; Bolard, J. Effects of aggregation and solvent on the toxicity of amphotericin B to human erythrocytes. *Antimicrob Agents Chemother* 1992, 36 (11), 2518-2522. DOI: 10.1128/aac.36.11.2518 From NLM. (7) Fernández-García, R.; Muñoz-García, J. C.; Wallace, M.; Fabian, L.; González-Burgos, E.; Gómez-Serranillos, M. P.; Raposo, R.; Bolás-Fernández, F.; Ballesteros, M. P.; Healy, A. M. Self-assembling, supramolecular chemistry and pharmacology of amphotericin B: Poly-aggregates, oligomers and monomers. *Journal of Controlled Release* 2022, 341, 716-732. (8) Torrado, J.; Espada, R.; Ballesteros, M.; Torrado-Santiago, S. Amphotericin B formulations and drug targeting. *Journal of pharmaceutical sciences* 2008, 97 (7), 2405-2425. (9) Barwicz, J.; Christian, S.; Gruda, I. Effects of the aggregation state of amphotericin B on its toxicity to mice. *Antimicrobial Agents and Chemotherapy* 1992, 36 (10), 2310-2315. (10) Joly, V.; Farinotti, R.; Saint-Julien, L.; Chéron, M.; Carbon, C.; Yeni, P. In vitro renal toxicity and in vivo therapeutic efficacy in experimental murine cryptococcosis of amphotericin B (Fungizone) associated with Intralipid. *Antimicrobial agents and chemotherapy* 1994, 38 (2), 177-183. (11) Sachs-Barrable, K.; Lee, S. D.; Wasan, E. K.; Thornton, S. J.; Wasan, K. M. Enhancing drug absorption using lipids: a case study presenting the development and pharmacological evaluation of a novel lipid-based oral amphotericin B formulation for the treatment of systemic fungal infections. *Advanced drug delivery reviews* 2008, 60 (6), 692-701. Stone, N. R.; Bicanic, T.; Salim, R.; Hope, W. Liposomal amphotericin B (AmBisome®): a review of the pharmacokinetics, pharmacodynamics, clinical experience and future directions. Drugs 2016, 76 (4), 485-500. (12) Hamill, R. J.; Sobel, J. D.; El-Sadr, W.; Johnson, P. C.; Graybill, J. R.; Javaly, K.; Barker, D. E. Comparison of 2 doses of liposomal amphotericin B and conventional amphotericin B deoxycholate for treatment of AIDS-associated acute cryptococcal meningitis: a randomized, double-blind clinical trial of efficacy and safety. *Clin Infect Dis* 2010, 51 (2), 225-232. DOI: 10.1086/653606 From NLM. Clemons, K. V.; Stevens, D. A. Comparative efficacies of four amphotericin B formulations—Fungizone, amphotec (Amphocil), AmBisome, and Abelcet—against systemic murine aspergillosis. *Antimicrob Agents Chemother* 2004, 48 (3), 1047-1050. DOI: 10.1128/aac.48.3.1047-1050.2004 From NLM. (13) Cornely, O. A.; Maertens, J.; Bresnik, M.; Ebrahimi, R.; Ullmann, A. J.; Bouza, E.; Heussel, C. P.; Lortholary, O.; Rieger, C.; Boehme, A.; et al. Liposomal amphotericin B as initial therapy for invasive mold infection: a randomized trial comparing a high-loading dose regimen with standard dosing (AmBiLoad trial). *Clin Infect Dis* 2007, 44 (10), 1289-1297. DOI: 10.1086/514341 From NLM. (14) Halperin, A.; Shadkchan, Y.; Pisarevsky, E.; Szpilman, A. M.; Sandovsky, H.; Osherov, N.; Benhar, I. Novel water-soluble amphotericin B-PEG conjugates with low toxicity and potent in vivo efficacy. *Journal of Medicinal Chemistry* 2016, 59 (3), 1197-1206. Liu, F.; Yang, L.; Li, Y.; Junier, A.; Ma, F.; Chen, J.; Han, H.; Glass, Z.; Zhao, X.; Kumamoto, C. A. In vitro and in vivo study of Amphotericin B formulation with quaternized bioreducible lipidoids. *ACS Biomaterials Science & Engineering* 2020, 6 (2), 1064-1073. Wang, X.; Mohammad, I. S.; Fan, L.; Zhao, Z.; Nurunnabi, M.; Sallam, M. A.; Wu, J.; Chen, Z.; Yin, L.; He, W. Delivery strategies of amphotericin B for invasive fungal infections. *Acta Pharmaceutica Sinica B* 2021, 11 (8), 2585-2604. Faustino, C.; Pinheiro, L. Lipid systems for the delivery of amphotericin B in antifungal therapy. *Pharmaceutics* 2020, 12 (1), 29. (15) Das, S.; Devarajan, P. V. Enhancing safety and efficacy by altering the toxic aggregated state of Amphotericin B in lipidic nanoformulations. *Molecular Pharmaceutics* 2020, 17 (6), 2186-2195. (16) Tiyaboonchai, W.; Limpeanchob, N. Formulation and characterization of amphotericin B-chitosan-dextran sulfate nanoparticles. *International journal of pharmaceutics* 2007, 329 (1-2), 142-149. (17) Gruda, I.; Milette, D.; Brother, M.; Kobayashi, G.; Medoff, G.; Brajtburg, J. Structure-activity study of inhibition of amphotericin B (Fungizone) binding to sterols, toxicity to cells, and lethality to mice by esters of sucrose. *Antimicrobial agents and chemotherapy* 1991, 35 (1), 24-28. Adams, M.; Kwon, G. S. Spectroscopic investigation of the aggregation state of amphotericin B during loading, freeze-drying, and reconstitution of polymeric micelles. *J. Pharm. Pharm. Sci* 2004, 7, 1-6. (18) Shi, C.; Guo, D.; Xiao, K.; Wang, X.; Wang, L.; Luo, J. A drug-specific nanocarrier design for efficient anticancer therapy. *Nat Commun* 2015, 6, 7449. DOI: 10.1038/ncomms8449. (19) Guo, D.; Shi, C.; Wang, L.; Ji, X.; Zhang, S.; Luo, J. Rationally designed micellar nanocarriers for the delivery of hydrophilic methotrexate in Psoriasis treatment. *ACS applied bio materials* 2020, 3 (8), 4832-4846. Wang, L.; Ji, X.; Guo, D.; Shi, C.; Luo, J. Facial Solid-Phase Synthesis of Well-Defined Zwitterionic Amphiphiles for Enhanced Anticancer Drug Delivery. *Molecular Pharmaceutics* 2021, 18 (6), 2349-2359. (20) Guo, D.; Shi, C.; Wang, X.; Wang, L.; Zhang, S.; Luo, J. Riboflavin-containing telodendrimer nanocarriers for efficient doxorubicin delivery: High loading capacity, increased stability, and improved anticancer efficacy. *Biomaterials* 2017, 141, 161-175. (21) Guo, D.; Ji, X.; Luo, J. Rational nanocarrier design towards clinical translation of cancer nanotherapy. *Biomedical Materials* 2021, 16 (3), 032005. (22) Luo, J.; Xiao, K.; Li, Y.; Lee, J. S.; Shi, L.; Tan, Y. H.; Xing, L.; Holland Cheng, R.; Liu, G. Y.; Lam, K. S. Well-defined, size-tunable, multifunctional micelles for efficient paclitaxel delivery for cancer treatment. *Bioconjug Chem* 2010, 21 (7), 1216-1224. DOI: 10.1021/bc1000033. (23) Todke, P. A.; Devarajan, P. V. In-silico approach as a tool for selection of excipients for safer amphotericin B nanoformulations. *Journal of Controlled Release* 2022, 349, 756-764. (24) Kamiński, D. M. Recent progress in the study of the interactions of amphotericin B with cholesterol and ergosterol in lipid environments. *European biophysics journal* 2014, 43 (10), 453-467. (25) Perez, M. J.; Briz, O. Bile-acid-induced cell injury and protection. *World journal of gastroenterology: WJG* 2009, 15 (14), 1677. (26) Alvarez, C.; Shin, D. H.; Kwon, G. S. Reformulation of Fungizone by PEG-DSPE Micelles: Deaggregation and Detoxification of Amphotericin B. *Pharm Res* 2016, 33 (9), 2098-2106. DOI: 10.1007/s11095-016-1948-7 From NLM. Shao, K.; Huang, R.; Li, J.; Han, L.; Ye, L.; Lou, J.; Jiang, C. Angiopep-2 modified PE-PEG based polymeric micelles for amphotericin B delivery targeted to the brain. *Journal of Controlled Release* 2010, 147 (1), 118-126. DOI: doi.org/10.1016/j.jconrel.2010.06.018. (27) Alberts B, J. A., Lewis J, et al., The Lipid Bilayer. In *Molecular Biology of the Cell* 4th ed.; New York: Garland Science, 2002. Yeagle, P. L. Cholesterol and the cell membrane. *Biochim Biophys Acta* 1985, 822 (3-4), 267-287. DOI: 10.1016/0304-4157 (85) 90011-5 From NLM. (28) Clemons, K. V.; Stevens, D. A. Comparison of Fungizone, Amphotec, AmBisome, and Abelcet for treatment of systemic murine cryptococcosis. *Antimicrobial Agents and Chemotherapy* 1998, 42 (4), 899-902.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What we claim is:

1. A nanocarrier drug delivery system comprising: a PEGylated telodendrimer, one or more hydrophobic groups on a dendritic periphery of said telodendrimer, and said nanocarrier having a core structure containing a plurality of micelles and at least one hydrophobic polyene therapeutic agent.

2. The nanocarrier drug delivery system of claim 1, wherein the PEGylated telodendrimer comprises oxyethylene repeating units having the following formula: $H(OCH_2CH_2)_nOH$, wherein n represents number of units and PEG has a molecular weight that ranges from about 2,000 dalton to about 20,000 dalton.

3. The nanocarrier drug delivery system of claim 1, wherein the dendritic periphery comprises branching units.

4. The nanocarrier drug delivery system of claim 3, wherein the branching units are at least one selected from the group consisting of: 2,6-diaminohexanoic acid (poly-lysine), 2,3-diamino propanoic acid, 2,4-diaminobutanoic acid, 2,5-diaminopentanoic acid (ornithine), (2-Amino-ethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid branching units.

5. The nanocarrier drug delivery system of claim 1, wherein the dendritic periphery comprises one or more hydrophobic groups.

6. The nanocarrier drug delivery system of claim 5, wherein the one or more hydrophobic groups are selected from the group consisting of, heptadecanoic acid (C17), oleic acid (OA), cholesterol (CHO), vitamin E (VE), deoxycholic acid (dCA), and cholic acid (CA).

7. The nanocarrier drug delivery system of claim 1, wherein the hydrophobic polyene therapeutic agent is amphotericin B (AmB).

8. The nanocarrier drug delivery system of claim 1, wherein the hydrophobic polyene therapeutic agent is at least one selected from the group consisting of amphotericin B (AmB), nystatin, candicidin, pimaricin, methyl partricin, and trichomycin.

9. The nanocarrier drug delivery system of claim 2, wherein PEGylated-telodendrimer is $PEG^{5k}C17_4$ having a hydrodynamic particle size distribution between 10-100 nm, the at least one hydrophobic polyene therapeutic agent is AmB having a hydrodynamic particle size distribution between 10-100 nm.

10. The nanocarrier drug delivery system of claim 7, wherein the ratio of telodendrimer to AmB is about 10:1.

11. The nanocarrier drug delivery system of claim 1, wherein micelles reduce molecular aggregation of the hydrophobic polyene therapeutic agent and the absence of UV-Vis absorption at 330 nm for the aggregated polyene.

12. The nanocarrier drug delivery system of claim 7, wherein micelles provide monomeric AmB release from nanocarrier drug delivery system.

13. The nanocarrier drug delivery system of claim 7, wherein the drug delivery system provides reduced cytotoxicity and increased antifungal potency.

14. A method of treating a subject in need thereof, comprising: injecting the nanocarrier drug delivery system of claim 1 into a subject in need thereof.

15. The method of claim 14, wherein the nanocarrier drug delivery system is characterized as pharmaceutically acceptable.

16. The method of claim 14, wherein the nanocarrier drug delivery system is injected in a therapeutically acceptable amount.

17. The method of claim 14, wherein the nanocarrier drug delivery system comprises a therapeutically acceptable amount of AmB.

18. A method of making a nanocarrier drug delivery system comprising: contacting a PEGylated linear telodendrimer, a dendritic polymer having branched polymers containing a focal point, a plurality of branched monomer units, and a plurality of hydrophobic end groups to provide a core structure containing a plurality of micelles and at least one hydrophobic polyene therapeutic agent.

19. The method of claim 18, wherein the PEGylated telodendrimer comprises oxyethylene repeating units having the following formula: $H(OCH_2CH_2)_nOH$ and n represents number of units, PEG molecular weight is from about 2,000 to about 20,000 Dalton, the branched polymers are polylysine, and one or more hydrophobic groups selected from the group consisting of: heptadecanoic acid (C17), oleic acid (OA), cholesterol (CHO), vitamin E (VE), deoxycholic acid (dCA), and lysine-cholic $acid_2$ ($lysCA_2$).

20. The method of claim 18, wherein the at least one hydrophobic polyene therapeutic agent is AmB.

* * * * *